US008012693B2

(12) United States Patent
Chong Conklin et al.

(10) Patent No.: US 8,012,693 B2
(45) Date of Patent: Sep. 6, 2011

(54) ANALYSIS OF CHEMICALLY CROSSLINKED CELLULAR SAMPLES

(75) Inventors: Bathsheba E. Chong Conklin, St. Paul, MN (US); Patrick J. Parks, Mendota Heights, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 1104 days.

(21) Appl. No.: 10/964,467

(22) Filed: Oct. 13, 2004

(65) Prior Publication Data

US 2005/0130121 A1    Jun. 16, 2005

Related U.S. Application Data

(60) Provisional application No. 60/530,127, filed on Dec. 16, 2003.

(51) Int. Cl.
*G01N 33/53* (2006.01)
*C12Q 1/68* (2006.01)
*C12Q 1/37* (2006.01)
*A61K 38/00* (2006.01)
*C07K 1/00* (2006.01)

(52) U.S. Cl. ............... 435/7.1; 435/6; 435/23; 530/300; 530/350

(58) Field of Classification Search ............... 435/6, 7.1, 435/91.1, 183, 23; 436/94; 536/23.1; 530/300, 530/350
See application file for complete search history.

(56) References Cited

U.S. PATENT DOCUMENTS

| | | | |
|---|---|---|---|
| 4,304,705 A | 12/1981 | Heilmann et al. | 260/30.4 |
| 4,451,619 A | 5/1984 | Heilmann et al. | 525/379 |
| 4,485,236 A | 11/1984 | Rasmussen et al. | 544/69 |
| 4,507,233 A * | 3/1985 | Saito et al. | 530/363 |
| 4,545,831 A | 10/1985 | Ornstein | 156/57 |
| 4,820,504 A | 4/1989 | Battifora | 424/3 |
| 4,914,022 A | 4/1990 | Furmanski et al. | 435/7 |
| 5,049,662 A | 9/1991 | Steeg et al. | 536/27 |
| 5,149,806 A | 9/1992 | Moren et al. | 544/72 |
| 5,204,219 A | 4/1993 | Van Ooij et al. | 430/272 |
| 5,258,041 A | 11/1993 | Guire et al. | 623/66 |
| 5,262,484 A | 11/1993 | Coleman et al. | 525/204 |
| 5,344,701 A | 9/1994 | Gagnon et al. | 428/304 |
| 5,403,902 A | 4/1995 | Heilmann et al. | 526/260 |
| 5,436,147 A | 7/1995 | Pegg et al. | 435/181 |
| 5,464,900 A | 11/1995 | Stofko, Jr. et al. | 524/838 |
| 5,500,251 A | 3/1996 | Burgoyne, Jr. et al. | 427/322 |
| 5,602,202 A | 2/1997 | Groves | 525/73 |
| 5,639,546 A | 6/1997 | Bilkadi | 428/331 |
| 5,728,915 A * | 3/1998 | Chang et al. | 800/2 |
| 5,753,437 A | 5/1998 | Steeg et al. | 435/6 |
| 5,843,644 A | 12/1998 | Liotta et al. | 435/6 |
| 5,843,657 A | 12/1998 | Liotta et al. | 435/6 |
| 5,883,155 A * | 3/1999 | Hoerner et al. | 523/122 |
| 6,010,888 A | 1/2000 | Liotta et al. | 435/100 |
| 6,136,592 A | 10/2000 | Leighton | 435/288 |
| 6,177,266 B1 | 1/2001 | Krishnamurthy et al. | 435/173 |
| 6,194,206 B1 | 2/2001 | West et al. | 435/375 |
| 6,204,030 B1 * | 3/2001 | Liotta et al. | 435/100 |
| 6,251,467 B1 * | 6/2001 | Liotta et al. | 427/2 |
| 6,251,516 B1 * | 6/2001 | Bonner et al. | 428/346 |
| 6,376,619 B1 * | 4/2002 | Halverson et al. | 525/330 |
| 6,395,483 B1 * | 5/2002 | Patil et al. | 435/65 |
| 6,548,607 B2 * | 4/2003 | Halverson et al. | 525/375 |
| 6,569,639 B2 * | 5/2003 | Liotta et al. | 435/40 |
| 6,573,338 B2 * | 6/2003 | Halverson et al. | 525/375 |
| 6,593,089 B2 * | 7/2003 | Patil et al. | 435/6 |
| 6,675,104 B2 | 1/2004 | Gavin et al. | 702/22 |
| 6,690,470 B1 * | 2/2004 | Baer et al. | 356/417 |
| 6,756,586 B2 | 6/2004 | Caprioli | |
| 6,897,072 B1 | 5/2005 | Rich et al. | 436/173 |
| 2002/0005205 A1 * | 1/2002 | Barry et al. | 128/898 |
| 2002/0009767 A1 * | 1/2002 | Muraca | 435/40 |
| 2002/0122917 A1 * | 9/2002 | Halverson et al. | 428/119 |
| 2003/0073145 A1 | 4/2003 | Caprioli | |
| 2006/0239968 A1 * | 10/2006 | Arap et al. | 424/93.2 |

FOREIGN PATENT DOCUMENTS

| | | |
|---|---|---|
| CA | 2 546 667 | 12/2006 |
| WO | WO 99/17094 A2 | 4/1999 |
| WO | WO 99/44062 A1 | 9/1999 |
| WO | WO 99/44063 A2 | 9/1999 |
| WO | WO 01/26460 A1 | 4/2001 |
| WO | WO 01/98352 A2 | 12/2001 |
| WO | WO 02/48674 A2 | 6/2002 |
| WO | WO 03/031031 A1 | 4/2003 |
| WO | WO 03/034024 A2 | 4/2003 |
| WO | WO 03/034024 A3 | 4/2003 |
| WO | WO 03/083107 A1 | 10/2003 |
| WO | WO 2004/080579 A2 | 9/2004 |
| WO | WO 2004/080579 A3 | 9/2004 |
| WO | WO 2006/127860 A2 | 11/2006 |
| WO | WO 2006/127861 A2 | 11/2006 |
| WO | WO 2006/138629 | 12/2006 |

OTHER PUBLICATIONS

Shi et al., Antigen retrieval techniques: current perspectives. The Journal of Histochemistry & Cytochemistry, 49, 931-937, 2001.*
Introduction of DTT from Fermentas life sciences. Printed on Mar. 2, 2009.*
Citrate buffer antigen retrieval protocol. Printed on Sep. 24, 2009.*
Lehrer et al., Intramolecular crosslinking of tropomyosin via disulfide bond formation: evidence for chain register. Proc. Natl. Acad. Sci, USA, 72, 3377-3381, 1975.*
H. Battifora; "Methods in Laboratory Investigation—The Multitumor (Sausage) Tissue Block: Novel Method for Immunohistochemical Antibody Testing"; Laboratory Investigation; vol. 55, No. 2, p. 244-248; 1986.
W. Wan et al.; "A rapid and efficient method for testing immunohistochemical reactivity of monoclonal antibodies against multiple tissue samples simultaneously"; Journal of Immunological Methods; 103 (1987) p. 121-129.
R. Miller et al.; "Multitumor "Sausage" Blocks in Immunohistochemistry—Simplified Method of Preparation, Practical Uses, and Roles in Quality Assurance"; A.J.C.P.—Anatomic Pathology; vol. 96, No. 2; p. 228-232; Aug. 1991.
J. Konen et al.; "Tissue microarrays for high-throughput molecular profiling of tumor specimens"; Nature Medicine; vol. 4, No. 7; Jul. 1998 p. 844-847.*

(Continued)

Primary Examiner — Frank W Lu
(74) Attorney, Agent, or Firm — Kevin W. Weber

(57) ABSTRACT

A method of analyzing cellular samples that include a chemically crosslinked analyte is provided. The analysis typically involves the use of mass spectrometry.

27 Claims, 10 Drawing Sheets

OTHER PUBLICATIONS

S. Shi et al.; "Antigen Retrieval Immunohistochemistry: Past, Present, and Future"; The Journal of Histochemistry & Cytochemistry; Vo. 45(3); 1997; p. 327-343.*

S. Shi et al.; "Development of An Optimal Protocol for Antigen Retrieval: A 'Test Battery' Approach Exemplified with Reference to the Staining of Retinoblastoma Protein (pRB) in Formalin-fixed Paraffin Sections"; Journal of Pathology; vol. 179; 1996; p. 347-352.*

S. Shi et al; "Antigen Retrieval Technique Utilizing Citrate Buffer or Urea Solution for Immunohistochemical Demonstration of Androgen Receptor in Formalin-fixed Paraffin Sections"; The Journal of Histochemistry and Cyrochemistry; vol. 41, No. 11; 1993; p. 1599-1604.*

S. Shi et al.; "Antigen Retrieval in Formalin-fixed, Paraffin-embedded Tissues: An Enhancement Method for Immunohistochemical Staining Based on Microwave Oven Heating of Tissue Sections"; The Journal of Histochemistry and Cyrochemistry; vol. 39, No. 6; 1991; p. 741-748.*

U. Schumacher; "Imunohistochemical assessment of cell proliferation in plant tissues using formaldehyde-fixed paraffin-embedded material"; Acta histochem; 97; 1995; p. 291-294.*

J. Oesterling; "Prostate Specific Antigen: A Critical Assessment of the Most Useful Tumor Marker for Adenocarcinoma of the Prostate"; The Journal of Urology; vol. 145; May 1991; p. 907-923.

G. Pinkus et al.; "Are Keratin Proteins a Better Tumor Marker than Epithelial Membrane Antigen?—A Comparative Immunohistochemical Study of Various Paraffin-Embedded Neoplasms Using Monoclonal and Polyclonal Antibodies"; A.J.C.P.; vol. 85, No. 3; Mar. 1986; p. 269-277.

R. Lai et al.; "Evaluation of Cytokeratin 19 Fragment (CYFRA 21-1) as a Tumor Marker in Malignant Pleural Effusion"; Jpn J. Clin. Oncol; vol. 29(9); 1999; p. 421-424.

S. Chaubal et al.; "Ep-CAM—A Marker for the Detection of Disseminated Tumor Cells in Patients Suffering from SCCHN"; Anticancer Research; vol. 19; 1999; p. 2237-2242.

S. Bernatchez et al.; "Histological characterization of a delayed wound healing model in pig"; Wound Repair and Regeneration; vol. 6, No. 3; May-Jun. 1998; p. 223-233.

B. Xu et al.; "Direct Analysis of Laser Capture Microdissected Cells by MALDI Mass Spectrometry"; J. Am Soc Mass Spectrom; vol. 13; 2002; p. 1292-1297.

P. Todd et al.; "Organic ion imaging of biological tissue with secondary ion mass spectrometry and matrix-assisted laser desorption/ionization"; J. Mass Spectrom; vol. 36; 2001; p. 355-369.

P. Chaurand et al.; "Direct Profiling of Proteins in Biological Tissues Sections by MALDI Mass Spectrometry"; Anal. Chem.; vol. 71, No. 23; Dec. 1, 1999; p. 5263-5270.

P. Chaurand et al.; "Imaging mass spectrometry: a new tool to investigate the spatial organization of peptides and proteins in mammalian tissue sections"; Chemical Biology; vol. 6; 2002; p. 676-681.

P. Chaurand et al.; "Profiling proteins from azoxymethane-induced colon tumors at the molecular level by matrix-assisted laser desorption/ionization mass spectrometry"; Proteomics; vol. 1; 2001; p. 1320-1326.

P. Chaurand et al.; "Direct profiling and imaging of peptides and proteins from mammalian cells and tissue sections by mass spectrometry"; Electrophoresis; vol. 23; 2002; p. 3125-3135.

M. Ahram et al.; "Evaluation of ethanol-fixed, paraffin-embedded tissues for proteomic applications"; Proteomics; vol. 3; 2003; p. 413-421.

Article from Expression Pathology, Inc. "Technology: To Array Archival Tissue Proteins is Key" from web site .expressionpathology.com/Technology.htm Printed Aug. 25, 2003 (2 pgs.).

Press Release printed Dec. 4, 2003 from the internet entitled "Affymetrix Enters into Collaboration with Arcturus to Enable Gene Expression Analysis on Paraffin-Embedded Tissues" (3 pgs.).

Emmery-Buck M.R. et al., "Laser Capture Microdissesction," Science, Nov. 8, 1996; 274(5289): 998-1001.

Pinkus et al., "Leu-M1 Immunoreactivity in Nonhematorpoietic Neoplasms and Myleoproliferative Disorders. An Immunoperoxidase Study of Paraffin Sections." Am. J. Clin. Pathol., Mar. 1986; 85(3): 278-82.

Shibutani et al., "Methacarn Fixation: A Novel Tool for Analysis of Gene Expressions in Parffin-Embedded Tissue Specimens," Lab. Invest., Feb. 2000, 80(2): 199-208.

Suarez-Quian CA et al., "Laser Capture Microdissesction of Single Cells from Complex Tissues," Biotechniquies, Feb. 1999; 26(2): 328-35.

Hibbs et al., "Differential Gene Expression in Ovarian Carcinoma Identification of Potential Biomarkers," American Journal of Pathology, 165(2):397-414 (Aug. 2004).

Matsuo et al., "Introduction to Modern Biological Mass Spectrometry," from Biological Mass Spectrometry: Present and Future, John Wiley & Sons, 1994, reprinted in J. Mass Spectrom., 35:114-130 (2000).

"Protein Prospector" [online]. University of California, San Francisco, Last modified May 10, 2002 [retrieved on Dec. 29, 2005]. Retrieved from the Internet:<http://prospector.ucsf.edu/>; 2 pgs.

"Mascot" [online]. Matrix Science Inc., Boston, MA, Copyright 2005 [retrieved on Dec. 29, 2005]. Last updated on Jun. 15, 2005. Retrieved from the Internet:<http://www.matrixscience.com/search_form_select.html>; 1 pg.

Redeker et al., "Combination of Peptide Profiling by Matrix-Assisted Laser Desorption/Ionization Time-of-Flight Mass Spectrometry and Immunodetection on Single Glands or Cells," Anal. Chem., 70:1805-1811 (1998).

Simone et al., "Technical Advance Sensitive Immunoassay of Tissue Cell Proteins Procured by Laser Capture Microdissection," American Journal of Pathology, 156(2):445-452 (Feb. 2000).

Srivastava et al., "ANX7, a candidate tumor suppressor gene for prostate cancer," PNAS, 98(8):4575-4580 (Apr. 10, 2001).

Yates, "Mass Spectrometry and the Age of the Proteome," J. Mass Spectrom., 33:1-19 (1998).

Bernardo, K. et al.; "Identification and discrimination of Staphylococcus aureus strains using matrix-assisted laser desorption/ionization—time of flight mass spectrometry"; Proteomics 2002, vol. 2 pp. 747-753.

Application Notes #MT-80 of Bruker Daltonics® entitled "Microorganism identification and classification based on MALDI-TOF MS fingerprinting with MALDI BioTyper" Mar. 2006; 4 pgs.

Hill, K. E. et al.; "Molecular analysis of microflora in chronic venous leg ulceration"; Journal of Medical Microbiology; Apr. 2003; vol. 52; No. 4; pp. 365-369.

Huang, C. et al.; Research Article entitled "In vivo detection of secreted proteins from wounded skin using capillary ultrafiltration probes and mass spectrometric proteomics"; Proteomics; 2006; vol. 6, pp. 5805-5814.

Kang, S. et al.; Research Article entitled "Proteomic analysis of injured spinal cord tissue proteins using 2-DE and MALDI-TOF MS"; Proteomics; 2006; vol. 6, pp. 2797-2812.

Liu, H. et al.; "Universal Sample Preparation Method for Characterization of Bacteria by Matrix-Assisted Laser Desorption of Ionization-Time of Flight Mass Spectrometry"; Applied and Environmental Microbiology, Mar. 2007; vol. 73, No. 6; pp. 1899-1907.

Liu, T. et al.; "High Dynamic Range Characterization of the Trauma Patient Plasma Proteome"; Molecular and Cellular Proteomics; May 9, 2006 as Manuscript M600068-MCP200; pp. 1-47.

Nanney, L. B. et al.; "Novel Approaches for Understanding the Mechanisms of Wound Repair"; Journal of Investigative Dermatology Symposium Proceedings; 2006; vol. 11; pp. 132-129.

Peng, X. et al.; "Proteomic approach to identify acute phase response-related proteins with low molecular weight in loach skin following injury"; Proteomics; 2004; vol. 4; pp. 3989-3997.

Pollins, A.C. et al.; "Proteomic Investigation of Human Burn Wounds by 2D-Difference Gel Electrophoresis and Mass Spectrometry"; Journal of Surgical Research; vol. 142; 2007; pp. 143-152.

Pusch, W. et al.; "Application of MALDI-TOF Mass Spectrometry in Screening and Diagnostic Research"; Current Pharmaceutical Designs; 2005; vol. 11; pp. 2577-2591.

Renoulet, Y. et al.; "Analysis of Protein Expression Profiles in Acute and Chronic Wounds by Multidimensional Protein Identification Technology (MUDPIT)"; (Presented at meeting for Second World Union of Wound Healing Societies in Paris, France Jul. 8-13, 2004) Printed in Wound Repair and Regeneration; vol. 13; No. 3; May-Jun. 2005; Cover pg A49 and Abstract 616 Only; p. A77.

Smole, S.C. et al.; "Sample preparation of Gram-positive bacteria for identification by matrix assisted laser desorption/ionization time-of-flight"; Journal of Microbiological Methods; vol. 48; 2002; pp. 107-115.

Yeoh-Ellerton, S.Y. et al.; "Iron and 8-Isoprostane Levels in Acute and Chronic Wounds"; The Journal of Investigative Dermatology; vol. 121, No. 4, Oct. 2003; pp. 918-925.

Wang, Y. et al.; "Bioinformatic Application in Proteomic Research on Biomarker Discovery and Drug Target Validation"; Current Bioinformatics; 2007; vol. 2; No. 1; pp. 11-20.

Lemaire, R. et al.; "Direct Analysis of MALDI Imaging of Formalin-Fixed, Paraffin-Embedded Tissue Sections"; Journal of Proteome Research, vol. 6; No. 4, 2007; pp. 1295-1305.

Caprioli, R.M. et al.; "Molecular Imaging of Biological Samples: Localization of Peptides and Proteins Using MALDI-TOF MS"; Analytical Chemistry; vol. 69, No. 23, Dec. 1, 1997; pp. 4751-4760.

Koomen, John M. et al.; "Mapping of surrogate markers of cellular components and structures using laser desorption/ionization mass spectrometry"; Journal of Mass Spectrometry; vol. 35, No. 2, 2000; pp. 258-264.

Ren et al. "Embedding of Tissue Sections Using Methylmethacrylate and Butyl Methacrylate", Journal of University of Hennan Medical Science, 25(4), 423, 1990.

* cited by examiner

ANALYSIS OF CHEMICALLY CROSSLINKED CELLULAR SAMPLES

CROSS-REFERENCE TO RELATED APPLICATIONS

The present application claims priority to U.S. Provisional Patent Application 60/530,127, filed on Dec. 16, 2003, which is incorporated herein by reference.

BACKGROUND

Microscopic examination and histopathologic diagnosis of both human and animal tissues has aided in the accuracy of medical diagnosis and treatment, as well as the advancement of research into diseases and their potential treatments. Advances in analytical techniques have provided the opportunity to understand the cellular mechanisms of disease and to select appropriate treatments. The identification of molecular markers of disease, such as tumor-specific antigens, has enabled diagnostic and prognostic assays to be developed that rely on the use of molecular probes (e.g., antibodies and nucleic acid probes) to detect these markers.

Historically, formalin fixation has been used with tissue in order to provide optimal specimen preservation for light microscopic examination of the preserved tissue. Chemical fixation with aldehydes is associated with denaturation that results from the crosslinking of pendant reactive amines. Formalin fixation results in methylene bridges between and among proteins, effectively reducing or removing the tertiary structure required for immune detection of proteins. Further, paraffin embedding is carried out at temperatures that can cause the loss of tertiary structure of the proteins thereby forming unfolded, but intact, proteins, reducing or removing enzymatic activity where it exists as well as removing, the structures (epitopes) required for immune detection.

Standard histological staining methods such as haematoxylin and eosin (H&E) generally can reveal only a limited amount of information. Current methods of microscopic evaluation can be extended to include such methods as morphometry, immunohistochemistry, in situ hybridization, etc. The identification and development of new clinically important molecular markers has been impeded by the slow and tedious process of determining the expression of these markers in large numbers of clinical specimens.

The natural progression of the data from the human genome project has been from single gene to multiple genes (genomics) and subsequently to identifying all proteins (proteomics) simultaneously. While "protein chips" carry the potential to measure concentrations, and perhaps function, at present immunohistochemistry is the only method capable of localization. Localization by immunohistochemistry is qualitative by nature, and semiquantitative at best using subjective evaluation by trained evaluators.

The ability to identify potential drug targets for potential treatment using immunohistochemistry has been amplified by the use of tissue microarrays (TMAs), a technology that involves the placement of many, typically 500 to 1000, tissue samples on a single microscope slide. Methods of grouping multiple tissue specimens on a single substrate have relied on manually cutting multiple paraffin-embedded tissue specimens and forming them into a composite block (see, e.g., Battifora et al., 1986, Lab. Invest. 55:244-248; U.S. Pat. No. 4,820,504) or into "straws" or "logs" from which transverse sections could be obtained (see, e.g., Wan et al., 1987, J. Immunol. Meth. 103:121-129; U.S. Pat. No. 4,914,022; Miller and Groothuis, 1991, A.J.C.P. 96: 228-232); and Kononen et al., 1998, Nat. Med. 4:844-7, which describes a technique for generating tissue arrays comprising hundreds of tumor specimens using punched samples from archival tissue blocks.

Tissue microarrays have the capacity to measure insoluble, large proteins such as extracellular matrix proteins, currently unavailable for analysis with standard mass spectrometric methods. Additionally, tissue microarrays complement protein microarrays, which have the potential to measure soluble proteins. However, a major difficulty with TMAs is the limited amount of data that comes with each "histospot" (the 0.15 cm diameter tissue section spotted onto the microarray).

DNA has been isolated from paraffin embedded tissue specimens following chemical fixation, typically with formalin. However, the methods involved in the formation of paraffin sections have heretofore excluded these sections from most of the molecular analytic methods, including mass spectrometry.

SUMMARY

The invention is directed to the analysis of cellular samples (e.g., cells, tissues, organs) that include a chemically crosslinked analyte (e.g., formalin-fixed proteins), wherein the sample is embedded in an organic solid material (e.g., paraffin). Typically and preferably such analysis involves the use of mass spectrometry, although this is not required.

More specifically, the present invention provides a method of analysis using mass spectrometry of chemically fixed, paraffin-embedded, tissues following reversal of at least a portion of the chemically crosslinked analytes (e.g., crosslinked proteins) to form decrosslinked analytes in a process commonly referred to as "antigen retrieval." Because mass spectrometry depends on the ionizability of a substance, and in the case of proteins, the ionizability of the proteins, it is possible to perform mass spectrometry on proteins since their primary structure is maintained and it is this primary structure that is analyzed using mass spectrometry (and associated methods). Because the methods such as mass spectrometry use known sequences of protein fragments to identify the proteins (e.g., peptide fingerprinting), mass spectrometry now can be successfully applied to articles derived from paraffin-embedded tissue samples.

Thus, the antigen retrieval step (decrosslinking) of the present invention unlocks a wealth of untapped proteomic information by enabling the analysis of previously chemically fixed paraffin-embedded tissue samples, including tissue microarrays (TMAs). In preferred embodiments, the use of mass spectrometric analysis techniques allow the simultaneous identification of multiple proteins.

In one aspect, the invention provides a method of analyzing an analyte. In this embodiment, the method includes: providing a cellular sample comprising a chemically crosslinked analyte, wherein the sample is embedded in an organic solid material; reversing at least a portion of the chemical crosslinks in the crosslinked analyte to form decrosslinked analyte; and analyzing the decrosslinked analyte.

In a particularly preferred embodiment, the cellular sample is a chemically fixed (e.g., formalin-fixed), paraffin-embedded tissue, and analyzing the analyte involves the use of mass spectrometry, and in particular, matrix assisted laser desorption ionization time of flight mass spectrometry (MALDI or MALDI-TOF).

Reversing the chemical crosslinks (i.e., breaking the bonds formed from chemically crosslinking the analyte or "decrosslinking") can occur through a variety of techniques. For example, it can occur through the application of energy in the presence of water or buffer at a range of pH values. The energy applied can be heat or radiation. Preferably, the conditions are selected in the reversing step such that substantially no naturally occurring bonds in the analyte are broken.

In certain embodiments, the method can further include cleaving at least a portion of the naturally occurring bonds (or other bonds not formed by the chemical fixative) in the decrosslinked analyte to form analyte fragments. For proteins, typically the cleavage occurs with an enzyme, such as trypsin, or by chemical cleaving reagents, such as cyanogen bromide. This cleavage step can occur prior to or after decrosslinking, although it is preferred that this step be carried out after decrosslinking. Chemical and/or enzymatic cleavage results in fragments of the analyte, e.g., peptides from proteins that are amenable to analysis by methods dependent on their primary structure, such as mass spectrometry. Furthermore, although not preferred, the decrosslinking step could also result in fragmentation of the analytes in addition to decrosslinking. In certain embodiments, analyzing the decrosslinked analyte can include identifying and/or quantifying the decrosslinked analyte.

In a particularly preferred embodiment, the present invention provides a method of analyzing an analyte, wherein the method includes: providing a chemically fixed, paraffin embedded, tissue section comprising one or more chemically fixed analytes; cleaving at least a portion of the chemically fixed bonds in the one or more analytes in the chemically fixed tissue; and analyzing the analyte using mass spectrometry.

A variety of different types of cellular samples (e.g., tissue and/or individual cells) can be used, including microarrays. In the preferred embodiment where the specimen under analysis is a microarray, at least one sample is from a human. In another aspect, at least one sample is from a plant. In another aspect, at least one sample is from an insect. In another aspect, at least one sample is from an individual having a disease. In a further aspect, the disease is a progressive disease and the sample is a microarray that includes a plurality of samples representing different stages in the progression of the disease. In one aspect, the disease is cancer. In another aspect, the disease is a respiratory disease, an infectious disease, an immune disease, a disease affecting reproductive organs (male or female), a cardiovascular disease, a disease affecting the endocrine system, a disease affecting the urinary system, a disease affecting the digestive system, a neurodegenerative disease and/or a neuropsychiatric disease. In the case of a chronic disease, the microarray can include samples representing both remission periods and exacerbation periods.

Similar variation in types and disease status can be applied to samples from a variety of experimental animals, e.g., mouse or rabbit. Individual tissues or collections of tissues, as in tissue microarrays, can be analyzed in a manner identical to human tissue, reflecting the utility of the method in drug target identification and/or validation. Preferably, the non-human animal is an animal model for a disease. In another aspect, the non-human animal includes at least one cell having therein exogenous nucleic acid (i.e., a nucleic acid which is not naturally found in the genome of an animal or plant).

In a further aspect, the non-human animal has been treated with a therapy for treating the disease.

In another method, the cellular sample is placed on a substrate that includes a polymeric material (e.g., a heat-shrink film), and the method further includes treating (e.g., by applying heat) the substrate such that the treated substrate has a projected surface area and a topographical surface area and said topographical surface area is greater than said projected surface area. The present invention also provides a tissue array that includes: a polymeric material with a projected surface area and a topographical surface area and said topographical surface area is greater than said projected surface area; and a plurality of tissue sections that include chemically fixed, paraffin-embedded, tissue. This embodiment is described in greater detail below in the section on substrates.

The following definitions are provided for specific terms that are used in the following written description.

The terms "comprises" and variations thereof do not have a limiting meaning where these terms appear in the description and claims.

As used herein, "a," "an," "the," "at least one," and "one or more" are used interchangeably. Thus, for example, a sample that comprises a chemically crosslinked analyte can be interpreted to mean that the sample includes "one or more" such analytes.

As used herein, "analyte" shall mean a molecule, compound, composition, or complex, either naturally occurring or synthesized, to be detected or measured in or separated from a sample of interest. Analytes include, without limitation, proteins, peptides, amino acids, fatty acids, nucleic acids, carbohydrates, hormones, steroids, lipids, vitamins, bacteria, viruses, pharmaceuticals, and metabolites. These analytes may or may not be capable of being crosslinked by a chemical fixative. For example, certain analytes, such as pharmaceuticals, metabolites, and vitamins, may not be chemically crosslinked, but can be analyzed in the method.

As used herein, "chemically crosslinked analyte" is an analyte that has been crosslinked using chemical means as a result of the addition of a chemical fixative capable of crosslinking, such as formalin or glutaraldehyde, for example. This does not include ethanol fixation. That is, although the analyte may have crosslinks within the molecule prior to addition of a chemical fixative, additional "chemical crosslinks" are incorporated into the analyte using a chemical crosslinking reagent (e.g., fixative).

As used herein, "a cellular sample" is one that is biological in nature in that it includes cells, whether they are individual cells, a part of a tissue, or a part of an organ. It is a recognized practice to isolate cells, e.g., from a biological fluid, form aggregates of the cells, e.g., by centrifugation, and to create chemically fixed paraffin embedded sections of the cell aggregates, commonly referred to as "cell blocks". The cells within the cell block reflect their tissues and organs of origin.

As used herein, a "tissue" is an aggregate of cells that perform a particular function in an organism and generally refers to cells and cellular material (e.g., such as extracellular matrix material) from a particular physiological region. The cells in a particular tissue can include several different cell types. A non-limiting example of this would be brain tissue that further includes neurons and glial cells, as well as capillary endothelial cells and blood cells.

As used herein, "chemically fixed, paraffin-embedded tissue section" refers to a chemically fixed, paraffin-embedded, material, such as formalin-fixed paraffin-embedded tissue. This term is often used conventionally to refer to tissues, cells, or organs embedded in paraffin. Herein, this is also referred to as "chemically fixed, paraffin-embedded cellular sample." While referred to as a "section," the embedded tissue or cell(s) can be generally of any shape or size, and are generally 20 microns or less in thickness.

As used herein, "a tissue microarray" is a microarray that includes a plurality of microscopic locations, each location comprising tissue cells and/or extracellular materials from tissues, or cells typically infiltrating tissues, where the morphological features of the cells or extracellular materials at each location are visible through microscopic examination. The term "microarray" implies no upper limit on the size of the tissue sample on the microarray, but merely encompasses a plurality of cellular (e.g., tissue) samples that, in one aspect, can be viewed using a microscope. As used herein "different types of tissues" refers to tissues which are preferably from different organs or which are at least from anatomically and histologically distinct sites in the same organ.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

The invention is directed to the analysis of cellular samples (e.g., cells, tissues, organs) that include a chemically crosslinked analyte (e.g., formalin-fixed tissue), wherein the sample is embedded in an organic solid material (e.g., paraffins or other media such as methylmethacrylate or other "plastic" embedding materials). Typically and preferably such analysis involves the use of mass spectrometry, although this is not required.

The cellular sample is one that is biological in nature in that it includes cells, whether they are individual cells, a part of a tissue, or a part of an organ. The cellular sample preferably includes a tissue section. Preferably, the cellular sample includes formalin-fixed tissue.

In a particularly preferred embodiment, the invention provides a method of analyzing a chemically fixed, paraffin-embedded, tissue section using mass spectrometry. The tissue samples analyzed by the method of the present invention can be evaluated in high throughput parallel analyses using MALDI mass spectrometry, enabling gene identification, protein identification, molecular profiling, selection of promising drug targets, sorting and prioritizing of expressed sequence array data, and the identification of abnormal physiological processes associated with disease.

Figure 1:
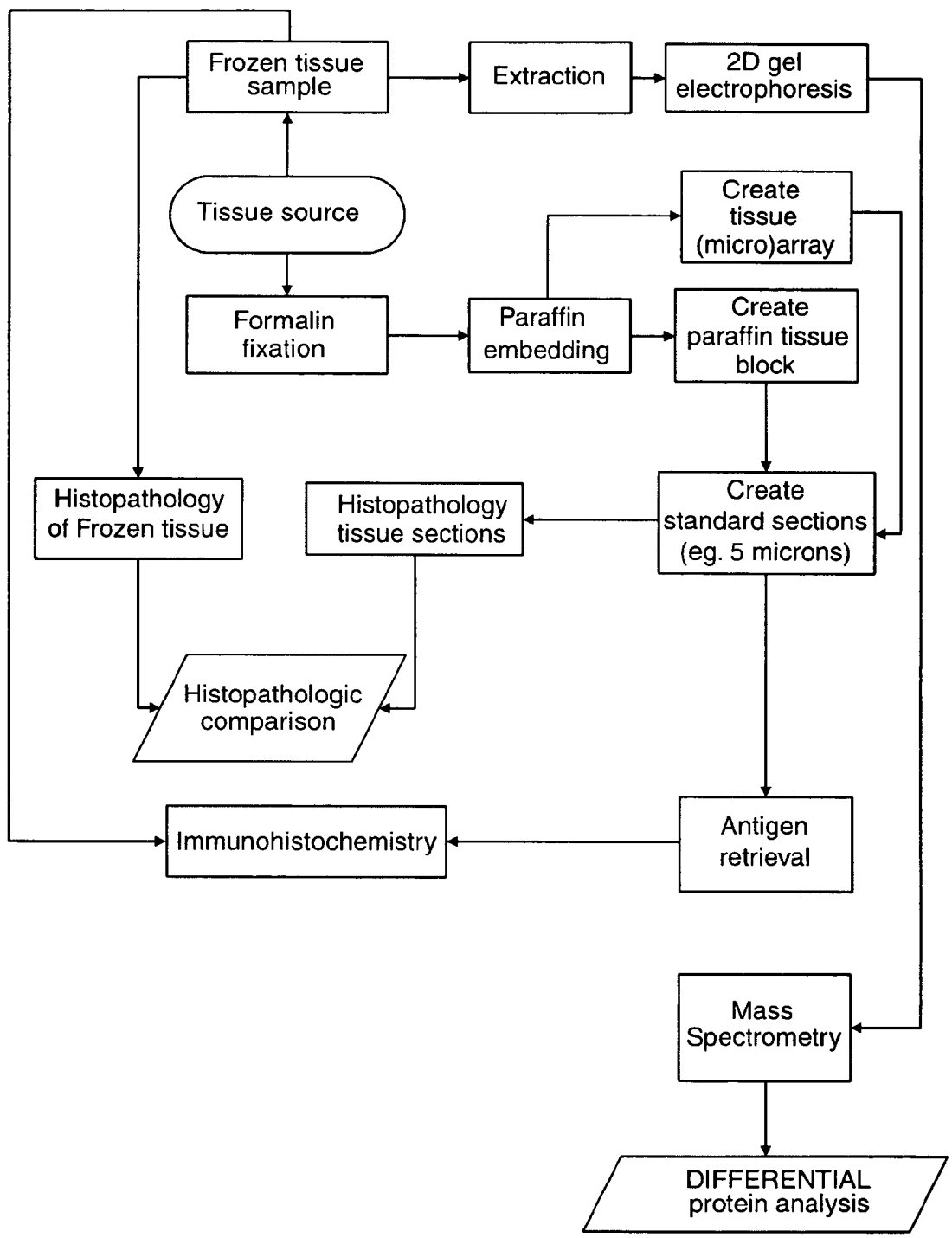
FIG. 1 is a schematic of a representative method used in the prior art.

A representation of conventional techniques that evaluate tissues is shown in FIG. 1. Typically, a tissue sample is either frozen or fixed (i.e., crosslinked) with formalin. A frozen sample can be directly subjected to immunohistochemistry or histopathology. Alternatively, a frozen tissue sample can be extracted, subjected to gel electrophoresis, and analyzed by mass spectrometry. A formalin-fixed tissue sample is typically embedded in paraffin, formed either into a block or a microarray, both of which are then formed into 5-micron thick sections. Such sections can then be directly subjected to histopathology. Alternatively, an analyte, most commonly a protein capable of inducing an immune response, can be subjected to a process that reverses at least a portion of the chemical crosslinks (i.e., the crosslinks formed by the formalin). This is conventionally referred to as "antigen retrieval" because in prior art methods such analytes are antigens, and because the method of analysis has conventionally been limited to antigen/antibody based techniques. Such "antigen" is then subjected to immunohistochemistry.

Such "decrosslinked analytes" have never been subjected to analysis by methods other than immunohistochemistry and histopathology because scientific literature in the fields of mass spectrometry and protein analysis have indicated that it is not possible to analyze substances, especially proteins, following fixation with chemical crosslinking fixatives such as formalin.

Figure 2:
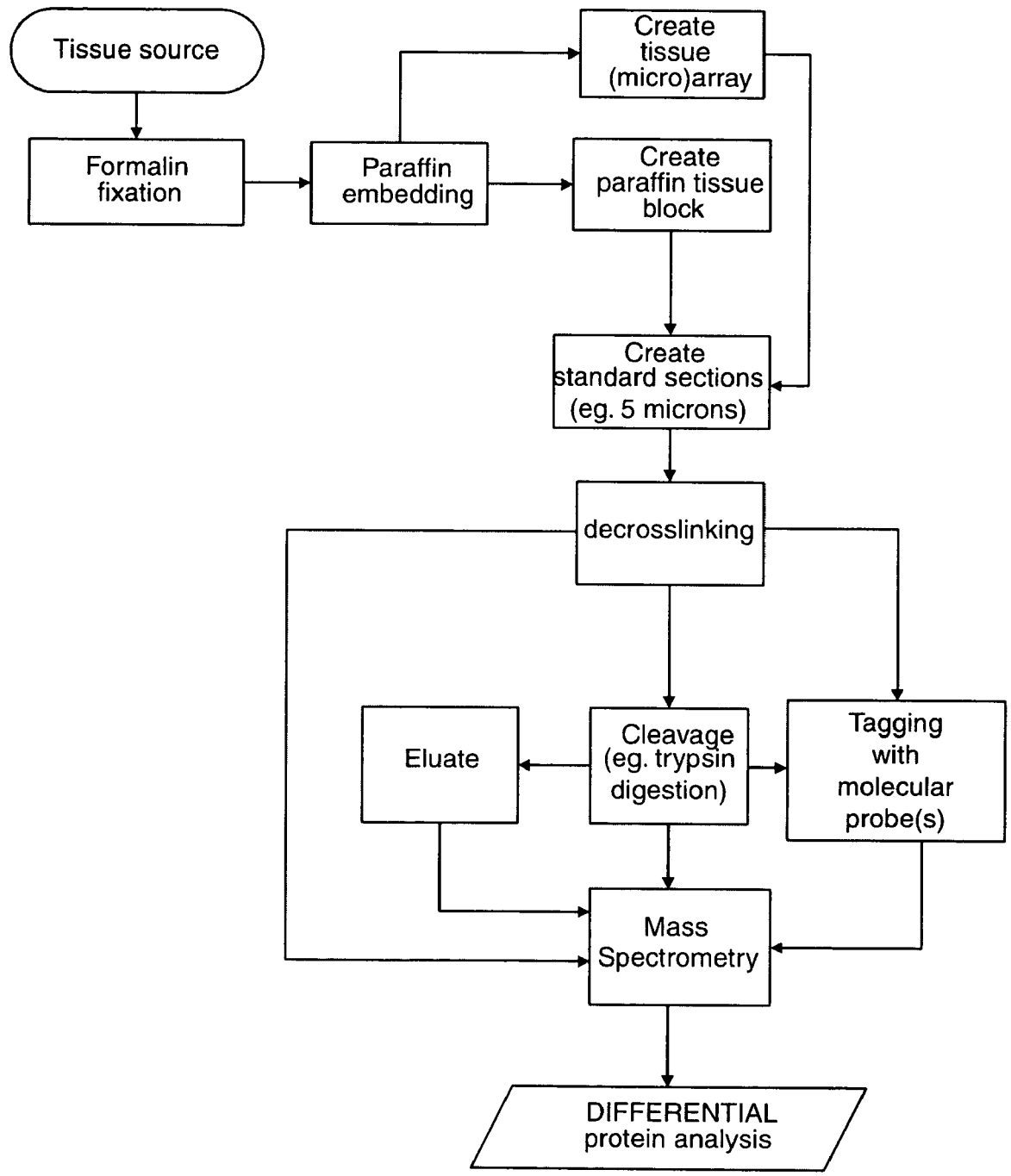
FIG. 2 is a schematic of a representative method of the present invention.
Figure 3:
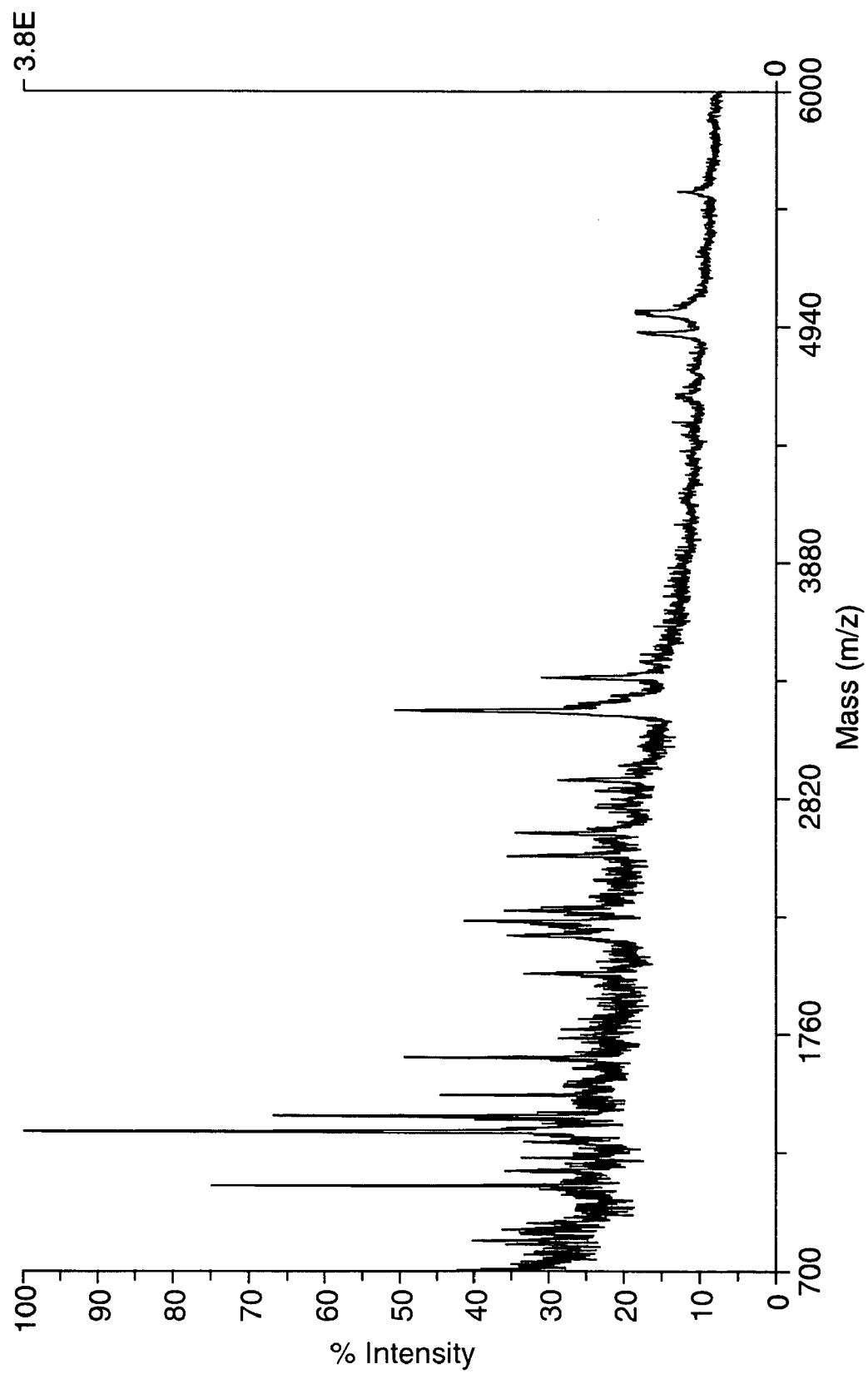
FIG. 3 is a representative graph of the mass spectra generated by Example 1, pig wound tissue.

A representation of a preferred embodiment of the present invention is shown in FIG. 2. In this preferred embodiment, a cellular sample (e.g., tissue sample) that has been chemically crosslinked (e.g., fixed with formalin), embedded in an organic solid material (e.g., paraffins), formed either into a block or a microarray, both of which are then typically formed into 5-micron thick sections, can be subjected to a method of the present invention that makes available an analyte by reversing at least a portion of the chemical crosslinks to form decrosslinked analyte. This is preferably accomplished while substantially no naturally occurring bonds (or other bonds present prior to crosslinking) in the analyte are cleaved.

If desired, the sample can be separated from the solid organic material (e.g., paraffin). This can occur prior to reversing the crosslinking. It can be accomplished by steam or any heating method. Preferably, this occurs at a temperature below that which causes decrosslinking.

A variety of techniques can be used to reverse at least a portion of the chemical crosslinks. Preferably, this is done through the application of energy. This can be accomplished in the presence of water or buffer at a range of pH values. The energy can be heat or radiant energy. Other methods can also be used including the use of chemical reagents, including acids such as citric acid. Such techniques are described in Shi S-R, Cote R J, Taylor C R., "Antigen retrieval immunohistochemistry: past, present, and future," *J. Histochem Cytochem* 1997; 45(3):327-343.

Referring to FIG. 2, this decrosslinked analyte can be directly subjected to analysis by a method such as mass spectrometry. Alternatively, the decrosslinked analyte can be subjected to a process for cleaving at least a portion of the naturally occurring bonds (or other bonds present prior to crosslinking) within the analyte. This can be done chemically or enzymatically (e.g., using trypsin), for example.

Optionally, the decrosslinked and/or cleaved analyte can be treated or tagged with a molecular probe (e.g., a dye) that can assist in enhancing or suppressing signal intensity of the analyte in a controlled manner. Such reagents and methods are well-known to one of skill in the art. For example, tagging the phosphopeptides can occur through various well-known methods such as Immobilized Metal Affinity Chromatography (IMAC). As used herein a "molecular probe" is any detectable molecule or molecule which produces a detectable signal upon reacting with a biological molecule. "Reacting" encompasses binding, labeling, or initiating an enzymatic reaction. Such detectable molecular probe can be recognized by a detectable binding reagent. In this context, a "detectable binding reagent" refers to an agent that specifically recognizes and interacts or binds with a molecular probe associated with an analyte one wishes to measure, wherein the agent has a property permitting detection when bound. "Specifically recognize and interact" means that a binding agent interacts with the molecular probe associated with the analyte one wishes to measure, to the substantial exclusion of other analytes also present in the sample. A detectable binding reagent can possess an intrinsic property that permits direct detection, or it can be labeled with a detectable moiety. As used herein, "detectable moiety" refers to a moiety that can be attached to a binding reagent that confers detection of the binding reagent by a particular method or methods. Detectable moieties include, but are not limited to, radiolabels (e.g., $^{32}P$, $^{35}S$, $^{125}I$, etc.), enzymes (e.g., alkaline phosphatase, peroxidase, etc.), fluorophores (e.g., fluorescein, amino coumarin acetic acid, tetramethylrhodamine isothiocyanate (TRITC), Texas Red, Cy3.0, Cy5.0, green fluorescent protein, etc.) and colloidal metal particles.

The method preferably includes cleaving at least a portion of other bonds (e.g., naturally occurring bonds or other bonds within the analyte prior to crosslinking) in the decrosslinked analyte to form analyte fragments. These analyte fragments can then be analyzed. Cleaving at least a portion of the bonds in the decrosslinked analyte includes contacting the decrosslinked analyte with an enzyme or chemical reagent. Preferably, an enzyme is used, such as trypsin, pepsin, pronase, chymotrypsin, and combinations thereof.

This cleavage step can occur prior to or after decrossinking, athough it is preferred that this step be carried out after decrosslinking. Chemical and/or enzymatic cleavage results in fragments of the analyte, e.g., peptides from proteins that are amenable to analysis by methods dependent on their primary structure, such as mass spectrometry. Furthermore, although not preferred, the decrosslinking step could also result in fragmentation of the analytes in addition to decrosslinking.

Again referring to FIG. 2, the digest can be directly subjected to a method of analysis, such as mass spectrometry, or an eluate of the digest can be removed and this can be subjected to a method of analysis.

The decrosslinked analyte can be analyzed using a variety of techniques, such as mass spectrometry, gel electrophoresis, enzyme linked immunoassay, DNA/RNA expression, or immunochemistry. Such techniques are well-known to one of skill in the art. Preferably, mass spectrometry is used.

The step of analyzing can be qualitative, which can include identifying the analyte (although identification is not necessarily required in analyzing). In certain embodiments, the step of analyzing can be quantitative.

Identifying an analyte can involve reading a unique identifier of the decrosslinked analyte. Such unique identifiers include, for example, peptide fingerprints for proteins. They can be "read" using techniques such as mass spectrometry.

Quantifying an analyte can involve fluorescent or isotope tagging. This can be done using techniques such as a stable isotope tag coupled with mass spectrometry.

It should be understood that cellular samples can include analytes that are not crosslinked and subsequently decrosslinked. For example, certain analytes, such as pharmaceuticals, metabolites, and vitamins, may not be chemically crosslinked. Such analytes can also be analyzed along with the decrosslinked analytes using the methods of the present invention.

Sample Preparation

In one aspect, the samples are tissue samples. Tissue samples can be obtained from chemically fixed, paraffin-embedded, tissue, and in particular, formalin-fixed, paraffin-embedded, tissue. A chemically-fixed, paraffin-embedded, tissue sample according to the invention typically includes one or more sections derived from tissue and/or cells. Preferably, each sample has at least one known biological characteristic (e.g., such as tissue type or cell type or patient source).

The tissue can be in the form of a tissue microarray, such as those described in Kononen et al., 1998, Nat. Med. 4:844-7. Generation of microarrays can be partially or fully automated using tissue microarrayers, such as the ones described in WO 99/44062, WO 99/44063, and U.S. Pat. No. 6,136,592.

Cells also can be obtained to provide one or more samples. Cells typically are formed into paraffin sections by centrifugation. Cells can be obtained from suspensions of cells from tissues (e.g., from a suspension of minced tissue cells, such as from a dissected tissue), from bodily fluids (e.g., blood, plasma, sera, and the like), from mucosal scrapings (e.g., such as from buccal scrapings or pap smears), and/or from other procedures such as bronchial ravages, amniocentesis procedures, and/or leukophoresis. In some aspects, cells are cultured first prior to being made part of the sample to expand a population of cells to be analyzed. Cells from continuously growing cell lines, from primary cell lines, and/or stem cells, also can be used.

In one aspect, a sample includes a plurality of tissues/cells from a single individual, i.e., the sample is microarray representing the "whole body" of an individual. Tissues can be selected from the group consisting of skin, neural tissue, cardiac tissue, liver tissue, stomach tissue, large intestine tissue, colon tissue, small intestine tissue, esophagus tissue, lung tissue, cardiac tissue, spleen tissue, pancreas tissue, kidney tissue, tissue from a reproductive organ(s) (male or female), adrenal tissue, and the like. Tissues from different anatomic or histological locations of a single organ can also be obtained, e.g., such as from the cerebellum, cerebrum, and medulla, where the organ is the brain. Some microarrays include samples representative of organ systems (i.e., comprising samples from multiple organs within an organ system), e.g., the respiratory system, urinary system, kidney system, cardiovascular system, digestive system, and reproductive system (male or female). In a preferred aspect, a whole body microarray additionally comprises a sample of cells from a bodily fluid of the patient (e.g., from a blood sample).

The microarray also can include a plurality of cells from individuals sharing a trait. For example, the trait shared can be gender, age, pathology, predisposition to a pathology, exposure to an infectious disease (e.g., HIV), kinship, death from the same disease, treatment with the same drug, exposure to chemotherapy, exposure to radiotherapy, exposure to hormone therapy, exposure to surgery, exposure to the same environmental condition (e.g., such as carcinogens, pollutants, asbestos, TCE, perchlorate, benzene, chloroform, nicotine and the like), the same genetic alteration or group of alterations, expression of the same gene or sets of genes (e.g., samples can be from individuals sharing a common haplotype, such as a particular set of HLA alleles), and the like.

Samples can be obtained from an individual with a disease or pathological condition, including, but not limited to: a blood disorder, blood lipid disease, autoimmune disease, bone or joint disorder, a cardiovascular disorder, respiratory disease, endocrine disorder, immune disorder, infectious disease, muscle wasting and whole body wasting disorder, neurological disorders including neurodegenerative and/or neuropsychiatric diseases, skin disorder, kidney disease, scleroderma, stroke, hereditary hemorrhage telangiectasia, diabetes, disorders associated with diabetes (e.g., PVD), hypertension, Gaucher's disease, cystic fibrosis, sickle cell anemia, liver disease, pancreatic disease, eye, ear, nose and/or throat disease, diseases affecting the reproductive organs, gastrointestinal diseases (including diseases of the colon, diseases of the spleen, appendix, gall bladder, and others), and the like. For further discussion of human acme diseases, see Mendelian Inheritance in Man: A Catalog of Human Genes and Genetic Disorders by Victor A. McKusick (12th Edition (3 volume set) June 1998, Johns Hopkins University Press, ISBN:0801857422). Preferably, samples from a normal demographically matched individual and/or from a non-disease tissue from a patient having the disease are arrayed on the same or a different microarray to provide controls.

In a preferred aspect, a sample is provided in a microarray format that includes a plurality of cells, which represent different stages of a cell proliferative disorder, such as cancer. In this context, "a cell proliferative disorder" is a condition marked by any abnormal or aberrant increase in the number of cells of a given type or in a given tissue. Cancer is often thought of as the prototypical cell proliferative disorder, yet disorders such as atherosclerosis, restenosis, psoriasis, inflammatory disorders, some autoimmune disorders (e.g., rheumatoid arthritis), are also caused by abnormal proliferation of cells, and are thus examples of cell proliferative disorders.

In one aspect, in addition to including samples, which comprise the primary target of the disease (e.g., such as tumor samples), the microarray includes samples representing metastases of a cancer to secondary tissues/cells. Preferably, the microarray also includes normal tissues from the same patient from whom the abnormally proliferating tissue was obtained. In some aspects, at least one microarray includes cells from a cell line of cancerous cells (either primary or continuous cell lines). Samples can be homogeneous, including a single cell type (e.g., as in a small format or ultrasmall format microarray), or can be heterogeneous, including at least one additional type of cell or cellular material in addition to abnormally proliferating cells (e.g., as in large format microarrays where samples are generally larger than 0.6 mm in diameter). For example, the sample can include abnormally proliferating cells and at least one of fibrous tissue, inflammatory tissue, necrotic cells, apoptotic cells, normal cells, and the like.

Although in a preferred aspect of the invention, the tissue and/or cell samples include human specimens, in one aspect of the invention, specimens from other organisms are used. In one aspect, tissues from non-human animals are used that provide a model of a disease or other pathological condition. When the sample represents specimens from an animal model of a chronic disease, the sample can be in the form of a microarray which includes specimens representing different stages of the disease, e.g., such as from animals in a remission period or an exacerbation period. The microarray can additionally, or alternatively, include tissues from a non-human animal having the disease or condition that has been exposed to a therapy for treating the disease or condition (e.g., drugs, antibodies, protein therapies, gene therapies, antisense therapies, combinations thereof, and the like). In some aspects, the non-human animals can include at least one cell containing an exogenous nucleic acid (e.g., the animals can be transgenic animals, chimeric animals, knockout or knock-in animals). Preferably, arrays from non-human animals include multiple tissues/cell types from such a non-human animal. In one aspect, tissues/cells at different stages of development are used.

In another aspect, samples from plants may be used, such as those discussed in Schumacher U., "Immunohistochemical assessment of cell proliferation in plant tissues using formaldehyde-fixed paraffin-embedded material," Acta Histochem. 1995 July:97(3):291-4. Samples may include microarrays that include plants in different stages of their life cycle and/or different types of plant tissues. In some aspects, the plant samples can include at least one cell containing an exogenous nucleic acid (e.g., the plants can be transgenic plants).

In one embodiment, a section of formalin-fixed, paraffin embedded, tissue is obtained and stained with H&E. The stained section is used as a guide to select a region on the tissue section for sampling. While in some aspects, staining with a standard tissue or cell stain such as H&E can be suitable to identify cells or tissue areas of interest, in other aspects, sections of the tissue are evaluated for the expression of one or more biological characteristics (e.g., such as the expression of a genotype, transcript, or peptide, polypeptide, or protein of interest) in the sample represented by the section. An area of interest can be identified which expresses or does not express a particular biological characteristic.

In one embodiment, the sample is prepared by slicing a section of the tissue sample (i.e., cutting transversely from the tissue sample with respect to the longitudinal axis of the sample) and allowed to fall onto a substrate without crumpling. Preferably, each tissue sample generates 150 to 300 sections from 2 to 20 microns thick. More preferably, sections are 4 to 12 microns in thickness.

In some embodiments, an adhesive film is placed on a surface of the tissue sample both to keep the section flat after it is sliced and to provide a surface on which to more easily move the section to a substrate without tearing or wrinkling the section. The section on its adhesive backing is then transferred to a substrate section side-down, and the adhesive film is peeled away from the section. Adhesive films and adhesive-coated slides are both obtainable from Instrumedics, Inc., Hackensack, N.J. (see, e.g., CRYOJAN Tape Transfer System).

Once placed on a substrate, the tissue sample is processed by reversing at least a portion of the chemical crosslinks (i.e., those crosslinks formed by a chemical crosslinking agent such as formalin. This is known conventionally as an antigen retrieval step. Such a process is described in Shi S- R, Cote R J, Taylor C R., "Antigen retrieval immunohistochemistry: past, present, and future," J. Histochem Cytochem 1997; 45(3):327-343. During this decrosslinking step, the chemical fixation is reversed typically through the application of heat in the presence of water. For example, during decrosslinking of formalin-fixed, paraffin embedded, tissue, the tissue sample is subjected to 100° C. steam in the presence of citric acid at 9.3 pH. As known by those skilled in the art, modification of the acid used, the temperature and/or the pH will result in varying degrees of reversal of the crosslinking and antigen retrieval. Other energy sources include radiation energy, such as microwave energy.

The tissue section may be subject to a process of crosslink reversal (conventionally referred to as antigen retrieval) either before or after affixation to a substrate. In preferred embodiments, the tissue section is affixed to a substrate such as a glass slide before the reversal of crosslinks (decrosslinking).

In a preferred embodiment, the decrosslinked analyte can then be treated with an enzyme or chemical reagent to cleave at least a portion of the naturally occurring bonds or bonds present before crosslinking in the analyte of interest, such as proteins or peptides. Preferably, this involves in situ digestion. Suitable enzymes for cleaving the analyte include, but are not limited to, trypsin, chymotrypsin, pronase, and pepsin. In one embodiment with formalin-fixed, paraffin-embedded, tissue, the enzyme is trypsin. Other agents for cleaving the bonds may also be employed, such as formic acid and cyanogen bromide. Such agents and techniques are well-known to one of skill in the art.

Methods of Use

In one aspect, samples analyzed according to the invention are used to assay the expression and/or form of a cancer-specific marker or tumor-specific antigen. As used herein, "a cancer-specific marker" or a "tumor-specific antigen" is an analyte that is expressed preferentially on cancer cells and tumor cells, respectively, and is not expressed or is expressed to small degree in non-cancer/tumor cells of an adult individual.

In this context, "difference in expression characteristics" or a gene which is "differentially expressed" refers to an increase or decrease in a measurable expression characteristic of a given polypeptide. A difference can be an increase or a decrease in a quantitative measure (e.g., amount of protein or RNA encoding the protein) or a change in a qualitative measure (e.g., location of the protein).

A cancer-specific marker is any analyte that is involved in or correlates with the pathogenesis of a cancer, and can act in a positive or negative manner, as long some aspect of its expression or form influences or correlates with the presence or progression of cancer. While in one aspect, expressed levels of an analyte provide an indication of cancer progression or recurrence, in another aspect of the invention, the expressed form of an analyte provides the indication (e.g., a cleaved or uncleaved state, a phosphorylated or unphosphorylated state).

The cancer-specific marker can be the product of a characterized gene, e.g., such as a cell growth-related polypeptide, which promotes cell proliferation, or can be uncharacterized or only partially characterized (e.g., identified through the use of molecular profiling methods described above). Non-limiting examples of cancer-specific markers include growth factors, growth factor receptors, signal transduction pathway participants, and transcription factors involved in activating genes necessary for cell proliferation.

The so-called tumor antigens are also included among the growth-related polypeptides. Tumor antigens are a class of protein markers that tend to be expressed to a greater extent by transformed tumor cells than by non-transformed cells. As such, tumor antigens can be expressed by non-tumor cells, although usually at lower concentrations or during an earlier developmental stage of a tissue or organism. Tumor antigens include, but are not limited to, prostate specific antigen (PSA; Osterling, 1991, J. Urol. 145: 907-923), epithelial membrane antigen (multiple epithelial carcinomas; Pinkus et al., 1986, Am. J. Clin. Pathol. 85: 269-277), CYFRA 21-1 (lung cancer; Lai et al., 1999, Jpn. J. Clin. Oncol. 29: 421-424) and Ep-CAM (pan-carcinoma; Chaubal et al., 1999, Anticancer Res. 19: 2237-2242). Additional examples of tumor antigens include CA125 (ovarian cancer), intact monoclonal immunoglobulin or light chain fragments (myeloma), and the beta subunit of human chorionic gonadotropin (HCG, germ cell tumors).

In further aspects of the invention, cancer progression can be detected and/or monitored by examining the expression of the activity of a cancer-specific marker. For example, in one aspect, the activity of telomerase is monitored in situ in samples. Methods of in situ detection of telomerase activity are known in the art and are described, for example, in U.S. Pat. No. 6,194,206.

The tissue samples can also be used in conjunction with, or to validate, results obtained through other types of the analyses with the same or other types of samples. For example, the methods of the present invention can be used in conjunction with, or instead of, analyses using in situ detection and visualization using immunohistochemistry; laser capture microdissection (LCM) of samples such as that described in PCT International Application Nos. WO 99/17094A2 and WO 01/98352A1; gel electrophoresis and others, all of which are described in PCT International Application No. WO 02/48674 A2.

Tissue samples prepared according to the present invention also can be used to identify drug targets whose interactions with one or a plurality of analytes are associated with disease. For example, a drug target can be a molecule that is overexpressed or underexpressed during a pathological process. By identifying drug targets, drugs can be screened for which can restore a cell's/tissue's normal physiological functioning. For example, where a drug target is a molecule, which is overexpressed or underexpressed, a suitable drug could be a molecule (e.g., a therapeutic antibody, polypeptide, or nucleic acid), which restores substantially normal levels of the drug target.

In one aspect, identifying diagnostic analytes is performed by determining which molecules on a microarray are substantially always present in a disease sample and substantially always absent in a healthy sample, or substantially always absent in a disease sample and substantially always present in a healthy sample, or substantially always present in a certain form or amount in a disease sample and substantially always present in a certain other form or amount in a healthy sample. By "substantially always" it is meant that there is a statistically significant correlation between the expression/form of the analyte or set of analytes and the presence of an aberrant physiological process, such as a disease.

Preferably, expression of a diagnostic analytes or set of analytes is examined in a microarray comprising tissues from a drug-treated patient and tissues from an untreated diseased patient and/or from a healthy patient. In this aspect, the efficacy of the drug is monitored by determining whether the expression profile of the diagnostic molecule(s) returns to a profile which is substantially similar (e.g., not significantly different as determined by routine statistical testing) to the expression profile of the same analyte(s) in a healthy patient or a patient who has achieved a desired therapeutic outcome. In one aspect of the invention, data relating to any, or all of, tissue type, stage of development or disease, patient history, family history, diagnosis, prognosis, medication, morphology, concurrent illnesses, expression of molecular characteristics (e.g., markers), and the like, are recorded and stored in a database, indexed according to the tissue sample obtained.

Substrate

The substrate facilitates the analysis of the tissue sample on the substrate surface using mass spectrometry by concentrating the mass of the sample on the substrate and/or selectively binding analytes within the sample. The size and shape of the substrate can be varied, depending on the size and shape of the desired tissue section or sample. Suitable substrates for use in the present invention include the miniaturized arrays described in U.S. Pat. Nos. 6,376,619; 6,548,607 and 6,573,338. High density, miniaturized arrays are desirable because the use of such arrays may dramatically increase efficiency with respect to limited or expensive samples when compared to standard arrays.

The substrate serves as highly effective substrate for use with mass spectrometry for several reasons. The substrates facilitate the affixation and concentration of the tissue and/or cell samples, with all of the attendant advantages of high density, including the ability to increase detection signal strength. In this context, "affix" shall include any mode of attaching a substance to a substrate. Such modes shall include, without limitation, covalent and ionic bonding, adherence, such as with an adhesive, and physical entrapment within a substrate.

Both before and after reduction of the surface area, the substrate can concentrate the analytes of interest in the tissue and/or cell sample, which results in greater sensitivity with the mass spectrometer, and particularly MALDI-TOF mass spectrometry, than standard preparation methods, i.e., such as metal plates. In many embodiments, such as those utilizing the linking agents described below (herein, "linking agent" shall mean any chemical species capable of affixing a "reactant" to the substrate), the substrate can stabilize matrix interactions with the deposited tissue and/or cell sample, and reduce the tendency for the matrix to sublime under vacuum conditions in the mass spectrometer. In some instances, the choice of polymeric material and linking agents for the substrate may selectively isolate the analyte of interest for detection by mass spectrometry.

The substrate, with the tissue section as treated above, can be reduced in surface area, either by application of heat when using heat-shrink material, or relaxation of the stretched substrate when using elastomeric material, as described in U.S. Pat. Nos. 6,376,619; 6,548,607 and 6,573,338. The reduced substrate with the attached tissue sample can then be analyzed using standard mass spectrometry techniques.

In one embodiment of the present invention, a polymeric substrate includes a major surface having a surface area. A tissue and/or cell sample is affixed to the major surface of the substrate. The surface area of the major surface is reduced, thereby increasing the density of a specific point on the substrate. In a preferred embodiment, the substrate is a biaxially oriented, heat shrink film. In another embodiment of the present invention, a heat shrink film is functionalized to create linking agents on the surface of the film for subsequent attachment of the tissue and/or cell sample. The surface area of the substrate surface may be reduced, thereby increasing the density of linking agents on the substrate. Preferably, the heat shrink surface is functionalized with azlactone linking agents.

In yet another embodiment of the present invention, an elastomeric substrate is stretched and functionalized to create linking agents on the surface of the substrate. The tissue section may be affixed to the substrate via linking agents. The substrate is subsequently allowed to relax, thereby reducing the surface area of the substrate to increase the density of linking agents on the substrate. A backing or other structure may be added to retain the substrate in the reduced orientation.

Many polymeric materials may be suitable for use as the substrate. However, in order to form the high surface area surface of the linking agent coating, as described more fully below, the materials are preferably capable of being oriented, i.e., films that shrink at least in one direction within the film plane when energy, preferably heat, is applied to the film for a specified period of time. Elastomeric materials, which are stretched at least in one direction prior to affixation of tissue and/or cell samples, constrained in the stretched state during affixation of the samples, and then allowed to recover, thereby reducing the projected surface area (i.e., the surface area for a surface as is calculated with respect to the plane encompassing the "x" and "y" axes of the surface) of the substrate surface from the stretched state, are also suitable for use in the present invention. The substrate material preferably is compatible with the reagents and conditions of the desired analytical methods, such as temperature and pH.

With respect to oriented films, shrinkage need not be equal in any two orthogonal directions within the film plane, although a substantially uniform shrinkage is preferred. In considering shrinkage as a function of direction in the film plane, substantial uniformity is preferred; that is, the film preferably shrinks in substantially the same amount in each direction, regardless of position on the film plane. If the film employed does not exhibit substantially uniform shrink characteristics, a registration indicator may be added.

While the starting substrate material of the present invention includes oriented films, the substrates of the present invention are generally relaxed, i.e., generally no longer oriented or, in fact, isotropic. A backing may be applied to the substrate to maintain the substrate in a less than oriented state. The backing may optionally include a release liner to permit the backing to be removed if desired.

The substrate provides a preferably non-porous surface upon which coatings and/or reactants may be affixed. Upon relaxation of the oriented substrate or reduction of the surface area of the major surface, the substrate provides support and integrity to the coatings and/or reactants thereon. In addition, the substrate maintains the relative spatial relationship of the tissue and/or cell sample.

In this context, "reactant" shall mean any chemical molecule, compound, composition or complex, either naturally occurring or synthesized, that is capable of binding an analyte in a sample of interest either alone or in conjunction with a molecule or compound that assists in binding the analyte to the substrate, such as, for example, a coenzyme. The reactants of the present invention are useful for chemical or biochemical measurement, detection, or separation. Accordingly, the term "reactant" specifically excludes molecules, compounds, compositions or complexes, such as ink, that do not bind analytes as described above. Examples of reactants include, without limitation, amino acids, nucleic acids, including oligonucleotides and cDNA, carbohydrates, and proteins such as enzymes and antibodies.

Preferred oriented films include biaxially oriented low-density polyethylenes; biaxially oriented linear low-density polyethylenes; and biaxially oriented ultra low-density polyethylenes. Biaxially oriented films are preferred because they exhibit shrinkage in two orthogonal in-plane directions (hereafter referred to as the "x" and "y" directions). Other oriented films that may be suitable for use in the present invention include uniaxially, biaxially, or multiaxially oriented films made by any process known to the art, including but not limited to melt-orientation; the blown film, bubble, double-bubble, and tubular processes; length orientation; the process of tentering; extension over a mandrel; thermoforming; and blow molding.

Polymers which may be employed in such films include, but are not limited to, polyethylenes, including high density polyethylene, low density polyethylene, linear low density polyethylene, ultra low density polyethylene, and copolymers of ethylene (including ethylene propylene copolymers and ethylene vinyl acetate copolymers); polyolefins, including isotactic polypropylene, syndiotactic polypropylene, and polymethylpentene; polyacetals; polyamides, including polyamide 6 and polyamide 66; polyesters, including polyethylene terephthalate, polybutylene terephthalate, and polyethylene naphthalate; halogenated polymers, including polyvinyl chloride, polyvinylidene chloride, polychlorotrifluoroethylene, polyvinyl fluoride, and polyvinylidene fluoride; styrene polymers, including general purpose polystyrene and syndiotactic polystyrene; cellulose esters, including cellulose acetate and cellulose propionate; polyketones, including polyetheretherketone and copolymers and terpolymers of carbon monoxide with ethylene and/or propylene; polycarbonates, including the polycarbonate of bisphenol A; phenyl-ring polymers, including polyphenylene sulfide; polysulfones; polyurethanes; polymers of acrylic and methacrylic acids and their esters; ionomers; and copolymers, blends, or layered structures of any of the above-named polymers. Oriented films of any of these polymers may be optionally cross-linked.

Examples of elastomeric materials that may be suitable for use in the present invention include natural rubber, polyisoprenes, polychloroprene, polyisobutylenes, polybutenes, nitrites, polyurethanes, silicones, random copolymers and terpolymers (such as ethylene-propylene copolymers and ethylene-propylene-diene monomer terpolymers), and block copolymers.

The substrate optionally includes a coating comprising linking agents. The linking agents are selected based on the tissue and/or cell sample to be affixed to the substrate and the application for which the sample will be used.

In some embodiments, the linking agents are coated onto the major surface of the substrate such that the coating is at least partially adhered to the substrate. The coating comprising linking agents has a projected surface area and a topographical surface area. The coating on the substrate generally is smooth in appearance. Accordingly, the projected surface area and the topographical surface area are substantially equivalent. In this context, "projected surface area" shall mean the surface area for a surface as is calculated with respect to the plane encompassing the "x" and "y" axes of the surface; and "topographical surface area" shall mean the surface area of a surface as is calculated with respect to the planes encompassing the "x", "y" and "z" axes of the surface, or in other words, a measurement of the surface features of the coating.

As described more fully below, upon relaxation of the substrate, the topographical surface area becomes greater than the projected surface area. The topographical surface area of the coating is at least two times greater, preferably at least five times greater than the projected surface area, and more preferably at least fifteen times greater than the projected surface area.

In a preferred embodiment, upon relaxation of the substrate, the coating of linking agents becomes undulated. While the undulations may be irregular with respect to any discernable pattern, it is contemplated that a regular pattern of undulations may be achievable in accordance with the methods of the present invention. In this context, "undulations—or—undulated" shall mean convoluted, wave-like forms. "Undulations—or—undulated" does not include structures such as reservoirs or microwells that are created by methods such as for example printing, embossing, casting, molding, laserscribing, photolithography, etching, mechanical scratching or scoring.

A coating of 0.1 micron to 10 microns is preferred, with a coating of less than 1 micron being preferred in order to minimize diffusion difficulties that may arise when using thicker coatings.

Preferred linking agents are azlactone moieties such as those provided by copolymers as taught in U.S. Pat. Nos. 4,304,705; 4,451,619; 5,262,484; 5,344,701; and 5,403,902. Especially preferred copolymers are those prepared using hydrophilic or water-soluble comonomers such as acrylamide and acrylamide derivatives, hydroxyethylacrylate and methacrylate, and the like. In addition to azlactone linking agents, copolymers including other linking agents may also be utilized. These include, for example, epoxy, carboxylic acid, hydroxyl, amine, N-hydroxysuccinimide, iso- and isothiocyanate, anhydride, aldehyde, and other groups, which are well known in the art for the immobilization of reactants. The copolymers comprising linking agents may be prepared by either step growth or chain growth polymerization processes as are well known in the art.

The coatings may be applied and may be crosslinked or otherwise treated to insolubilize, modify the glass transition temperature (Tg) or modify the adhesion properties of the coating. For example, copolymers that have a low Tg may be formulated with a cross-linker in order to raise the Tg of the resultant coating. The coatings can be applied to the substrate by any of several conventional means known in the art, such as extrusion coating, die coating, dip coating, air-knife coating, gravure coating, curtain coating, spray coating, use of wire wound coating rods, and the like. Coatings may be made from solution, followed by removal of solvent, or by hot melt coating of 100% solids formulations.

Adhesion of the coating to the substrate may be improved, if desired, by any of the methods known to one skilled in the art. These methods include various pre-treatments to or coatings on the major surface, such as corona or plasma treatment, or by application of primers. Suitable primers include, without limitation, polyethylenimine, polyvinylidenechloride, primers such as those described in U.S. Pat. No. 5,602,202, and colloidal dispersions of inorganic metal oxides in combination with ambifunctional silanes such as described in U.S. Pat. Nos. 5,204,219, 5,464,900, and 5,639,546. Other methods of increasing adhesion of copolymers to polyolefin substrates are disclosed in U.S. Pat. No. 5,500,251.

The linking agents may be coated substantially over the entire area of a surface of the substrate, such as the major surface, or in spots that may be in a regular or irregular pattern on such surface. In the latter case, upon relaxation of the substrate, the topographical surface area of each spot will be greater than the projected surface area of such spot. Alternatively, more than one polymeric layer comprising linking agents may be coated on the substrate. A first coating of linking agents may be overcoated by a second coating comprising linking agents in order to obtain undulations.

In addition to the linking agents, the substrate may further be coated with reactants to create binding sites that aid in affixing the tissue and/or cell sample, or to create a tissue and/or cell microarray. The type of reactant to be used will vary according to the application and analyte of interest. In this context, "binding site" shall mean a discrete location on a substrate wherein reactants when used are affixed thereto. A single binding site may include a quantity of one or more of the same reactants affixed to the substrate.

Substrates that further include a mask layer may also be useful, such as the mask layers described in U.S. Pat. Nos. 6,395,483 and 6,593,089. A mask layer of metal, such as titanium, deposited between the polymeric material and the coating may improve signal-to-noise ratios, or otherwise improve the quality of analysis.

The tissue section is affixed to the substrate by any number of processes known in the art may be used to affix the tissue section to the substrate. It is understood that the mode of affixation may vary in accordance with the intended analysis and selection of materials.

The tissue section may be affixed prior to, during or after reduction of the major surface or relaxation of the substrate. However, it is preferred to affix the sample prior to reduction of the major surface or relaxation of the substrate in order to take advantage of the concentration of sample density that may be achieved.

The substrate starting material is at least partially oriented. Oriented films exhibit an area shrinkage reduction that is dependent in part on the degree of elongation of the film during orientation thereof. The area shrinkage reduction is a measure of the area shrinkage of the film from its oriented, pre-shrunken dimensions to its dimensions after energy has been applied to shrink the film. An area shrinkage reduction of twenty-five percent (25%) is suitable for use in the present invention.

Depending on the mode of affixation, the substrate may be further prepared by functionalizing the surface to create linking agents. The type of functionalization will depend on the type of substrate and reactant(s). For example, in one embodiment using an oriented film, such as oriented polyethylene, the linking agents are azlactone moieties. In addition to the azlactone copolymers-set forth above, suitable azlactone functional compounds include those such as are disclosed in U.S. Pat. Nos. 4,485,236 and 5,149,806.

One method of functionalizing the surface includes acid washing the substrate followed by the addition of a bis-amino molecule to create an amine-functional surface, to which azlactone-linking agents are affixed. Other processes for functionalizing polymers are known in the art and are suitable to the extent they can be employed to create linking agents for affixation of reactants, for example, the hetero bifunctional cross-linking agents disclosed in U.S. Pat. No. 5,436,147. The linking agents preferably remain substantially affixed to the substrate after reduction of the surface area of the major surface and further preferably are not substantially degraded by the reduction of the surface area.

One skilled in the art should also appreciate that a variety of approaches to rendering the surfaces of elastomeric materials chemically reactive are known and may be employed in the present invention to the extent their use creates linking agents on the substrate for subsequent affixation of reactants. The linking agents preferably remain substantially affixed to the substrate after reduction of the surface area of the major surface or relaxation of the substrate and further preferably are not substantially degraded by such reduction or relaxation. One example of such an approach for treating surfaces for analyte attachment is described in U.S. Pat. No. 5,258,041.

It is preferred that the tissue sample be introduced to the substrate in a known pattern for purposes of registration. The initial starting position of the sample, for example, should be known in order to correlate this position with the final position once the substrate size has been reduced to the dimension that will be employed in conducting the assay. Examples include labeling, use of dyes, etc.

After affixation of the tissue sample to the substrate, preferably the major surface thereof, or in certain instances, after functionalization of the substrate to create linking agents, the substrate is relaxed and the surface area of the major surface of the substrate is reduced by the application of energy, such as heat, in the case of oriented films and by the relaxation of the stretching force in the case of elastomeric materials. The increase in density of the tissue and/or cell samples, and reactants and linking agents if present, may be dramatic. This increased density of sample is advantageous where an increased signal for detection is desired, for example when performing mass spectrometry.

With respect to oriented films, the reduction is preferably effected by the application of heat. However, any mode that results in the reduction of the surface area of the major surface may be sufficient for purposes of this invention. Preferably, the mode of size alteration, such as the application of heat, does not substantially impair the activity of the reactants. In the present invention, heat may be employed to shrink a substrate having a tissue section affixed thereto without destroying the ability to analyze the resultant substrate using mass spectrometry.

With respect to elastomeric materials, the surface area reduction may be achieved by releasing the force that is holding the material in the stretched condition. The substrate may be subsequently treated to hold the substrate in the reduced format. Alternatively, a backing or other physical means may be affixed to the substrate to hold it in the size altered format. After size alteration of the substrate, the substrate, if desired, may be treated to retain the substrate in the reduced surface area state. Such treatment includes cross-linking the substrate. Alternatively, physical modes may be used, such as affixing a backing to the substrate.

EXAMPLES

These examples are merely for illustrative purposes only and are not meant to be limiting on the scope of the appended claims. All parts, percentages, ratios, etc. in the examples and the rest of the specification are by weight, unless noted otherwise. Furthermore, molecular weights in the examples and the rest of the specification are weight average molecular weights, unless noted otherwise.

TABLE 1

| Example | FIG. | Description of Tissue Sample |
|---|---|---|
| 1 | 3 | Pig wound tissue - A repairing full thickness wound, created in 1998 as part of a preclinical study (Bernatchez, SF, PJ Parks, DM Grussing, SL Matalas, GS Nelson, Histological characterization of a delayed wound healing model in pig. Wound Rep. Reg. 6: 223–233, 1998) on animal model development for chronic wounds. |
| 2 | 4 & 5 | Prostate cancer tissue. Sample taken from a tissue microarray, Cancer Screen 2A, catalog ID: LS-SCA2A; commercially available from LifeSpan Biosciences, Inc., Seattle, WA. |
| 3 | 6 & 7 | Breast cancer tissue. Sample taken from a tissue microarray, Cancer Screen 2A, catalog ID: LS-SCA2A; commercially available from LifeSpan Biosciences, Inc., Seattle, WA. |
| 4 | 8 | Ovarian cancer tissue. Sample taken from a tissue microarray, Cancer Screen 2A, catalog ID: LS-SCA2A; |

TABLE 1-continued

| Example | FIG. | Description of Tissue Sample |
|---|---|---|
| | | commercially available from LifeSpan Biosciences, Inc., Seattle, WA. |
| 5 | 9 | Colon cancer tissue. Sample taken from a tissue microarray, Cancer Screen 2A, catalog ID: LS-SCA2A; commercially available from LifeSpan Biosciences, Inc., Seattle, WA. |
| 6 | 10 | Lung cancer tissue. Sample taken from a tissue microarray, Cancer Screen 2A, catalog ID: LS-SCA2A; commercially available from LifeSpan Biosciences, Inc., Seattle, WA. |
| 7 | 11 | Plant tissue. Sample taken from a tissue microarray, Cancer Screen 2A, catalog ID: LS-SCA2A; commercially available from LifeSpan Biosciences, Inc., Seattle, WA. |

For each example a sample of formalin fixed paraffin embedded tissue was taken and sectioned. A 4-micron thick section was mounted on film prepared as described in U.S. Pat. No. 6,376,619 Example No. 14. Examples 2-7 were not mounted on a film as described above, but rather were already sectioned since they were purchased as a tissue microarray. Next, during the antigen retrieval step, the formalin-fixed paraffin embedded tissue was subjected to 100° C. steam in the presence of citric acid at 9.3 pH. After the antigen retrieval step the tissue was digested by treatment in situ with lyophilized trypsin (T8658, commercially available from Sigma, St. Louis, Mo.) that was dissolved in 50 mM ammonium bicarbonate (Sigma) at pH 8.3 to a final concentration of 1.0 µg/µL, and incubated at 37° C. for 8 hours. The digested solution was removed and stored at 4° C. until analysis time. For example 1, the film was shrunk 25-fold in the x and y dimensions with a heat gun (HG-501A, Master Appliance Corp., Racine, Wis.) and adhered to a milled-out sample target plate by double-sided tape (3M, St. Paul, Minn.). Additionally for Example 1, a matrix solution of a-cyano-hydroxy-cinnamic acid (Sequazyme Kit, Applied Biosystems, Foster City, Calif.) was added to the film.

After air-drying, the prepared peptides were fingerprinted by using matrix assisted laser desorption ionization time-of-flight mass spectrometry (MALDI-TOF MS). Analyses were performed on examples 1-7 using a Voyager DE-STR (Applied Biosystems, Framingham, Mass.) in reflector and linear modes with positive ionization and an accelerating potential of either 20 or 25 kV. The instrument was calibrated with peptide and protein standards from Sequazyme Kit (Applied Biosystems) for mass accuracy. The nitrogen laser has a wavelength of 337 ηm, and the instrument was set to acquire 150 spectra per sample spot. The laser beam has a linear spot diameter of approximately 150-200 µm. The spectra were then summed and examples are shown in FIGS. 3, 4, 6, 8-11.

Protein Database Searching Procedure

For protein identification, peptide masses observed in the mass spectra of examples 1-3 were entered into publicly available protein database-search engines such as Protein Prospector (http://prospector.ucsf.edu) and MASCOT (http://www.matrixscience.com). The amino acid sequence coverage for these proteins from the observed peptides ranges from (approximately) 25 to 75%. Protein hits with highest probability score were tabulated as indicated in Tables 2-4. Table 2 shows a list of proteins identified with their isoelectric point molecular weights associated with Example 1, pig wound tissue. Table 3 shows a list of proteins identified with their isoelectric point molecular weights associated with Example 2, prostate cancer tissue. Table 4 shows a list of proteins identified with their isoelectric point molecular weights associated with Example 3, breast cancer tissue.

TABLE 2

Pig wound tissue
Proteins Identified From Electronic Databases With Their Isoelectric Point Molecular Weight (pI)

| Protein | Isoelectric point Molecular Weight (pI) |
|---|---|
| Adrenodoxin reductase | 9.32 |
| ATP synthase B chain, mitochondrial | 9.14 |
| Beta crystalline B3 (beta B3 crystalline) | 6.36 |
| Beta B3 crystalline | 6.07 |
| Casein kinase I, gamma 3 isoform | 9.39 |
| Collagen alpha 1 (II) chain precursor [Segment 1 of 2] | 8.97 |
| Cyclin dependent kinase 5 activator | 9.44 |
| Cyclin dependent kinase 5 activator 1 precursor (tau protein kinase II 23 kD subunit) | 9.44 |
| Cytochrome C oxidase polypeptide IV precursor | 9.32 |
| Cytochrome P450 (11 beta)-3 | 9.51 |
| Cytochrome P450 11 beta | 9.41 |
| Cytochrome P450 11B1 precursor | 9.43 |
| Cytochrome P450(C21) (M12918) | 8.53 |
| Epidiymal secretory protein E1 precursor (EPV20) | 8.20 |
| Ferredoxin-NADP + reductase (EC 1.18.1.2), long form precursor Gilal fibrillary acidic protein, astrocyte (GFAP) | 8.61 |
|  | 5.30 |
| Glucagon precursor | 6.11 |
| H+ transportin ATPase (EC 3.6.1.35 chain A, vacuolar | 5.42 |
| IgM heavy chain constant region | 5.68 |
| Immunoglobulin heavy chain constant region | 5.25 |
| Interferon beta-1 precursor | 5.95 |
| LP2-Fatty acid binding protein, epidermal (Differentiation associated lipid binding protein LP2) | 7.58 |
| LP2 (U55188) | 7.58 |
| Luteinizing hormone beta subunit prepeptide | 8.30 |
| Lutropin beta chain precursor (Luteinizing hormone beta subunit) (LSH-beta) | 8.00 |
| Lysozyme C precursor | 7.55 |
| Methylmalonate-semialdehyde dehydrogenase (acylating), mitochondrial precursor (MMSDH) | 8.29 |
| MHC class I heavy chain | 6.95 |
| MHC class II | 8.37 |
| MHC class II beta-chain | 6.14 |
| MHC class II DQB precursor (AF037315) | 6.66 |
| NADH adrenodoxin oxidoreductase, mitochondrial precursor | 8.67 |
| NADH ubiquinone oxidoreductase 30 kD subunit precursor | 6.54 |
| NADH ubiquinone oxidoreductase B18 subunit (complex I-B18) (CI-B18) | 8.35 |
| Proactivator polypeptide precursor [contains saposinA, saposin B, (sphingolipid activator protein 1)] | 5.13 |
| Prosaposin | 5.08 |
| Put. S-antigen C-terminus | 5.75 |
| RAC-alpha serine/threonine kinase (protein kinase B) | 5.57 |
| Rieske iron-sulfur protein precursor | 9.47 |
| S-adenosylmethionine decarboxylase proenzyme | 5.71 |
| Steroid 11beta-mono oxygenase (EC1.14.15.4) cytochrome P450 11B1-3 precursor | 9.51 |
| Steroid 11beta-mono oxygenase (EC1.14.15.4) cytochrome P450 11B1-2 precursor | 9.41 |
| Tau protein kinase (EC 2.7.1.135) II 23K chain precursor | 9.40 |

TABLE 2-continued

Pig wound tissue
Proteins Identified From Electronic Databases With Their Isoelectric Point Molecular Weight (pI)

| Protein | Isoelectric point Molecular Weight (pI) |
|---|---|
| T-cell receptor beta chain variable segment | 6.06 |
| UDP-glucose 6-dehydrogenase | 7.51 |
| Vacuolar ATP synthase catalytic subunit A, ubiquitous isoform | 5.42 |
| Vacuolar H ATPase subunit 70 kD | 5.47 |
| Vitamin D3 receptor | 6.18 |
| Voltage dependent calcium channel beta2B subunit | 8.36 |
| Zeta-crystallin | 8.77 |

TABLE 3

Prostate cancer tissue
Proteins Identified From Electronic Databases With Their Isoelectric Point Molecular Weight (pI)

| Protein | Isoelectric point Molecular Weight (pI) |
|---|---|
| KIAA1160 protein [Homo sapiens] | 5.17 |
| S100 calcium binding protein A11 (calgizzarin) [Homo sapiens] | 6.56 |
| Bcl-2 binding component 6 [Homo sapiens] | 10.12 |
| Solute carrier family 4 sodium bicarbonate cotransporter-like member 10 [Homo sapiens] | 6.05 |
| Myosin heavy chain beta-subunit | 6.75 |
| DRB1 transplantation antigen - human (fragment) | 4.58 |
| Phosphodiesterase 7A [Homo sapiens] | 8.94 |
| Nuclear autoantigen [Homo sapiens] | 10.61 |
| Mitochondrial intermediate peptidase [Homo sapiens] | 6.60 |
| Truncated steroid 21-hydroxylase [Homo sapiens] | 7.88 |
| Hypothetical protein DKFZp761G1515.1 - human (fragment) | 9.35 |
| 13 kD differentiation-associated protein - human (fragment) | 8.82 |
| Immunoglobulin heavy chain variable region [Homo sapiens] | 8.53 |
| ORF 2~no start codon [Homo sapiens] | 6.25 |
| BM023 [Homo sapiens] | 7.79 |
| PTE1 [Homo sapiens] | 7.68 |
| Peroxisomal acyl-coenzyme A thioester hydrolase 1 (Peroxisomal long-chain acyl-coA thioesterase 1) (HIV-Nef associated acyl coA thioesterase) (Thioesterase II) | 7.23 |
| PRO1181 [Homo sapiens] | 10.36 |
| Serine/threonine protein phosphatase with EF-hand motifs 2 isoform b; protein phosphatase with EF hands 2 [Homo sapiens] | 8.60 |
| Immunoglobulin heavy chain variable region [Homo sapiens] | 6.08 |

TABLE 4

Breast cancer tissue
Proteins Identified From Electronic Databases With Their Isoelectric Point Molecular Weight (pI)

| Protein | Isoelectric point Molecular Weight (pI) |
|---|---|
| Cationic trypsinogen [Homo sapiens] | 10.14 |
| Chain A, Structure Of The Cul1-Rbx1-Skp1-F Boxskp2 Scf Ubiquitin Ligase Complex | 6.37 |
| Coronin, actin binding protein, 1C; coronin, actin-binding protein, 1C; coronin 1C [Homo sapiens] | 6.65 |
| HSPC065 [Homo sapiens] | 5.53 |
| Hypothetical protein DKFZp434N035 [Homo sapiens] | 8.95 |
| Hypothetical protein DKFZp762H186.1 - human (fragment) | 8.34 |
| Immunoglobulin heavy chain third complementarity-determiningregion [Homo sapiens] | 6.43 |
| Immunoglobulin heavy chain variable region [Homo sapiens] | 8.91 |
| Immunoglobulin heavy chain VHDJ region [Homo sapiens] | 8.98 |
| Immunoglobulin lambda light chain variable region [Homo sapiens] | 5.82 |
| Immunoglobulin light chain variable region [Homo sapiens] | 8.68 |
| MHC class II antigen HLA-DR-beta 3 [Homo sapiens] | 9.12 |
| Mitochondrial malate dehydrogenase, precursor [Homo sapiens] | 8.92 |
| Myosin light chain kinase [Homo sapiens] | 5.52 |
| Paraoxanase-3 [Homo sapiens] | 5.24 |
| PDCD6IP protein [Homo sapiens] | 6.13 |
| Pheromone receptor [Homo sapiens] | 9.23 |
| PREDICTED: similar to Osteotesticular phosphatase; protein tyrosine phosphatase receptor type V; protein tyrosine phosphatase receptor type W; protein tyrosine | 5.98 |
| Serine protease inhibitor, Kazal type 4; gastrointestinal peptide [Homo sapiens] | 7.57 |
| Type XVIII collagen [Homo sapiens] | 9.26 |
| Ubiquitin-conjugating enzyme [Homo sapiens] | 7.71 |
| Ubiquitin-conjugating enzyme E2L 6 isoform 1; ubiquitin-protein ligase; ubiquitin carrier protein; retinoic acid induced gene B protein [Homo sapiens] | 7.71 |
| Unnamed protein product [Homo sapiens] | 9.65 |

Figure 4:
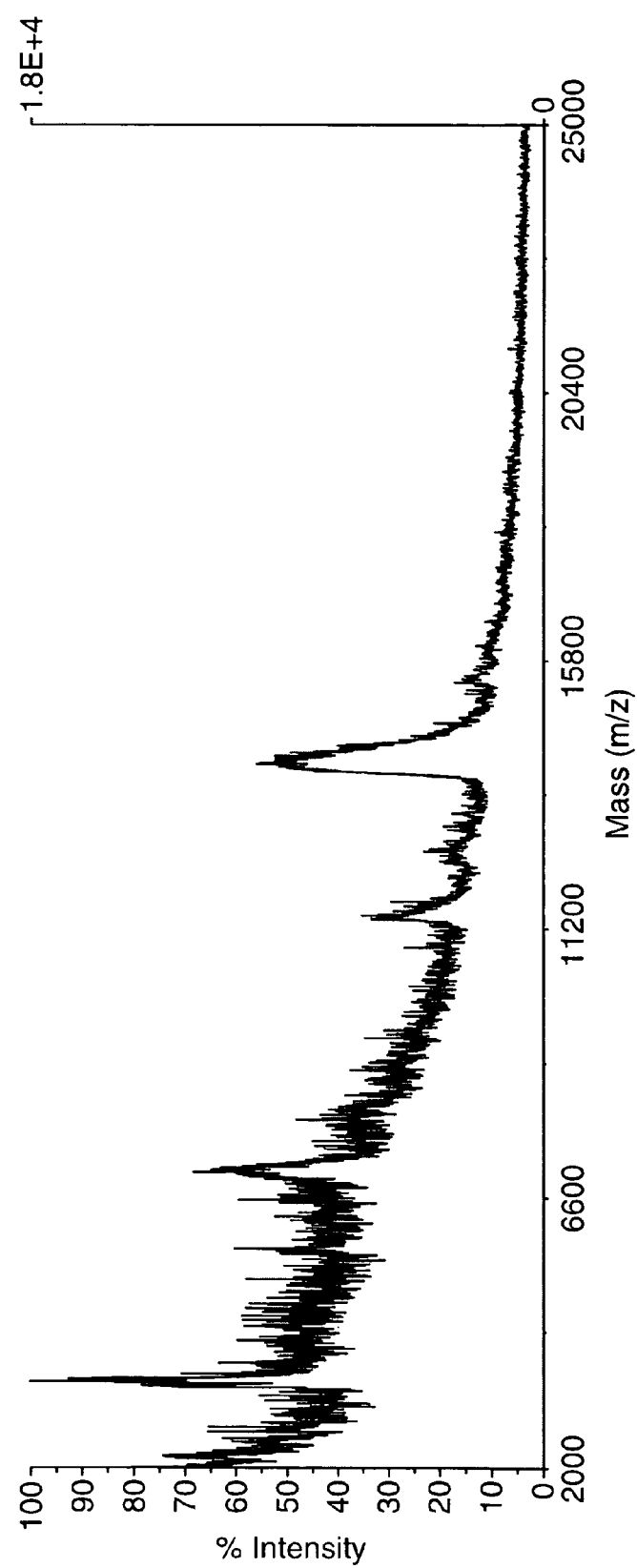
FIG. 4 is a representative graph of the mass spectra generated by Example 2, prostate cancer tissue.
Figure 5:
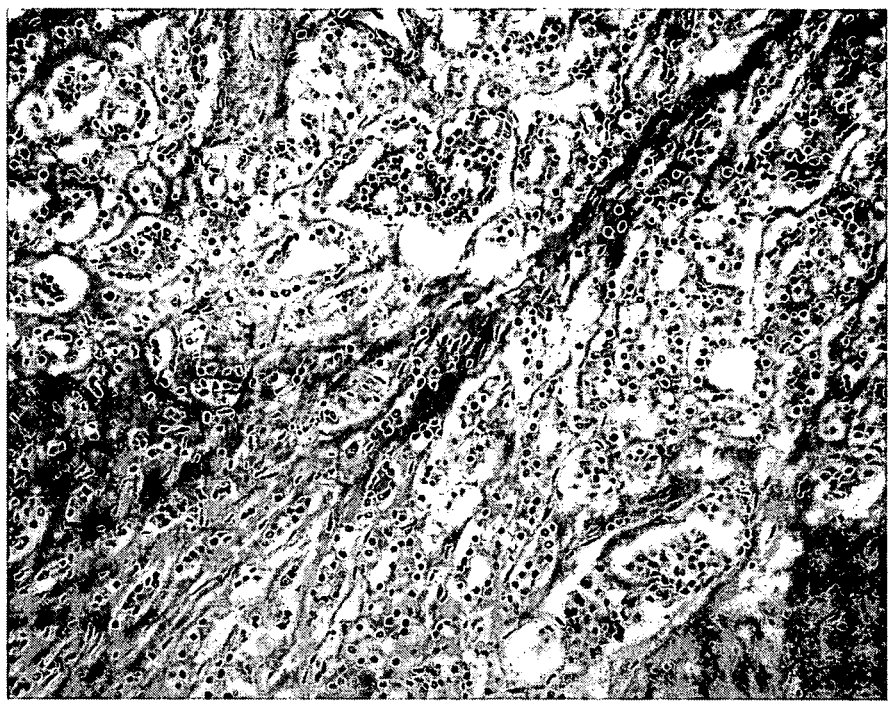
FIG. 5 is a photomicrograph of the prostate cancer tissue of Example 2.
Figure 7:
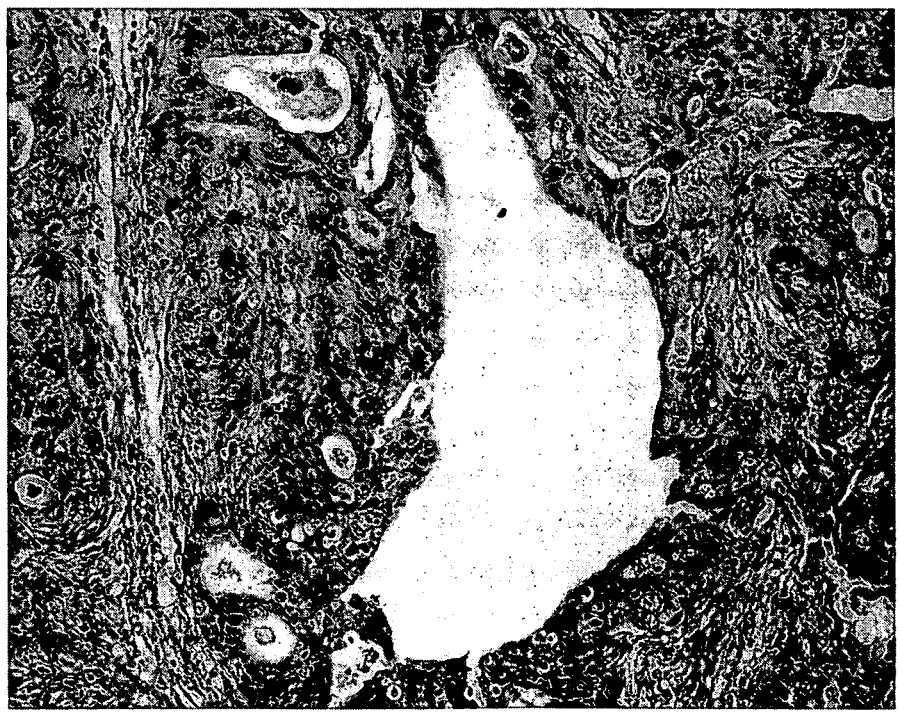
FIG. 7 is a photomicrograph of the breast cancer tissue of Example 3.
Figure 6:
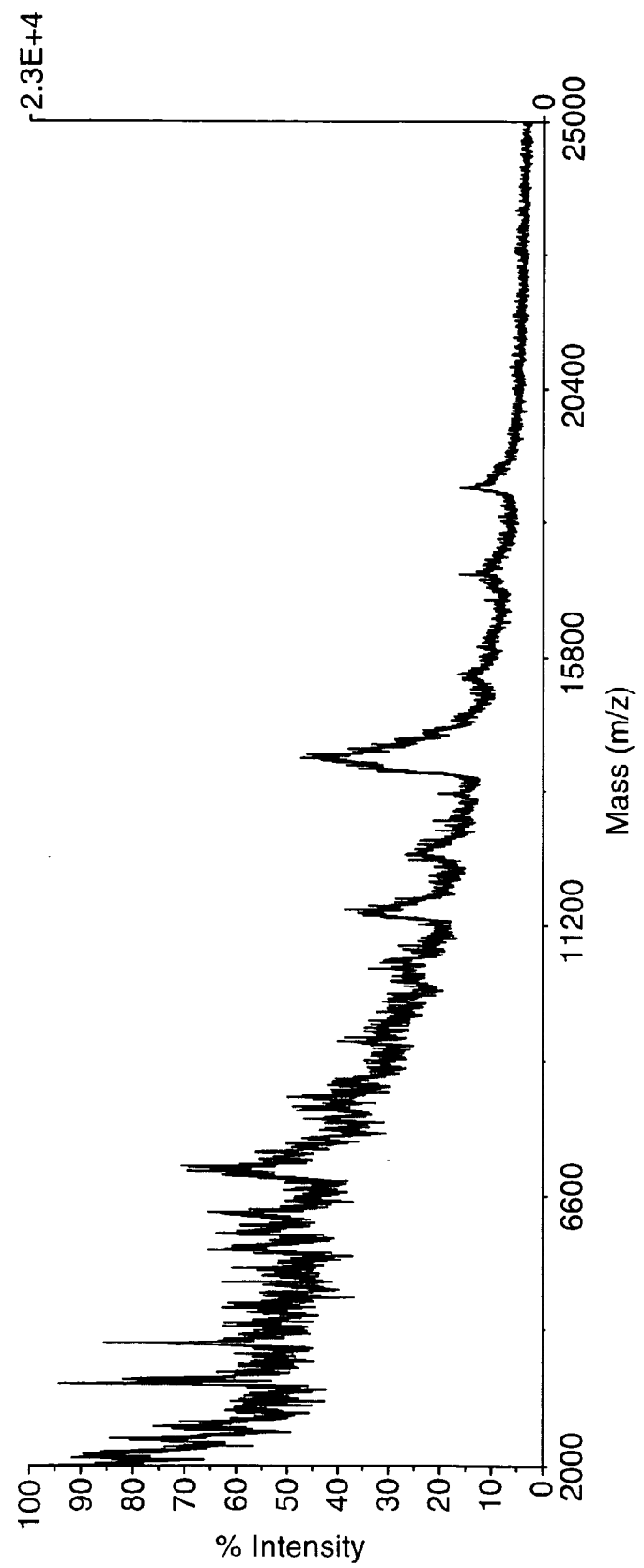
FIG. 6 is a representative graph of the mass spectra generated by Example 3, breast cancer tissue.
Figure 8:
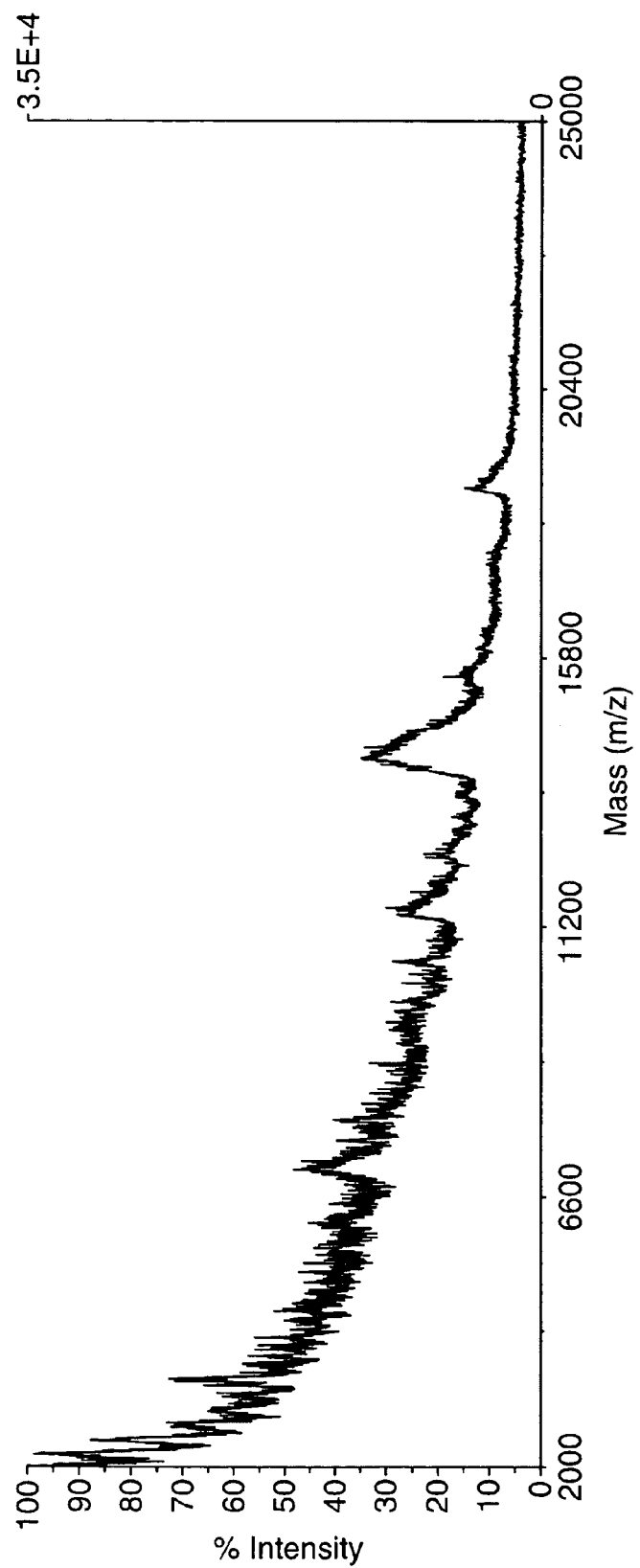
FIG. 8 is a representative graph of the mass spectra generated by Example 4, ovarian cancer tissue.
Figure 9:
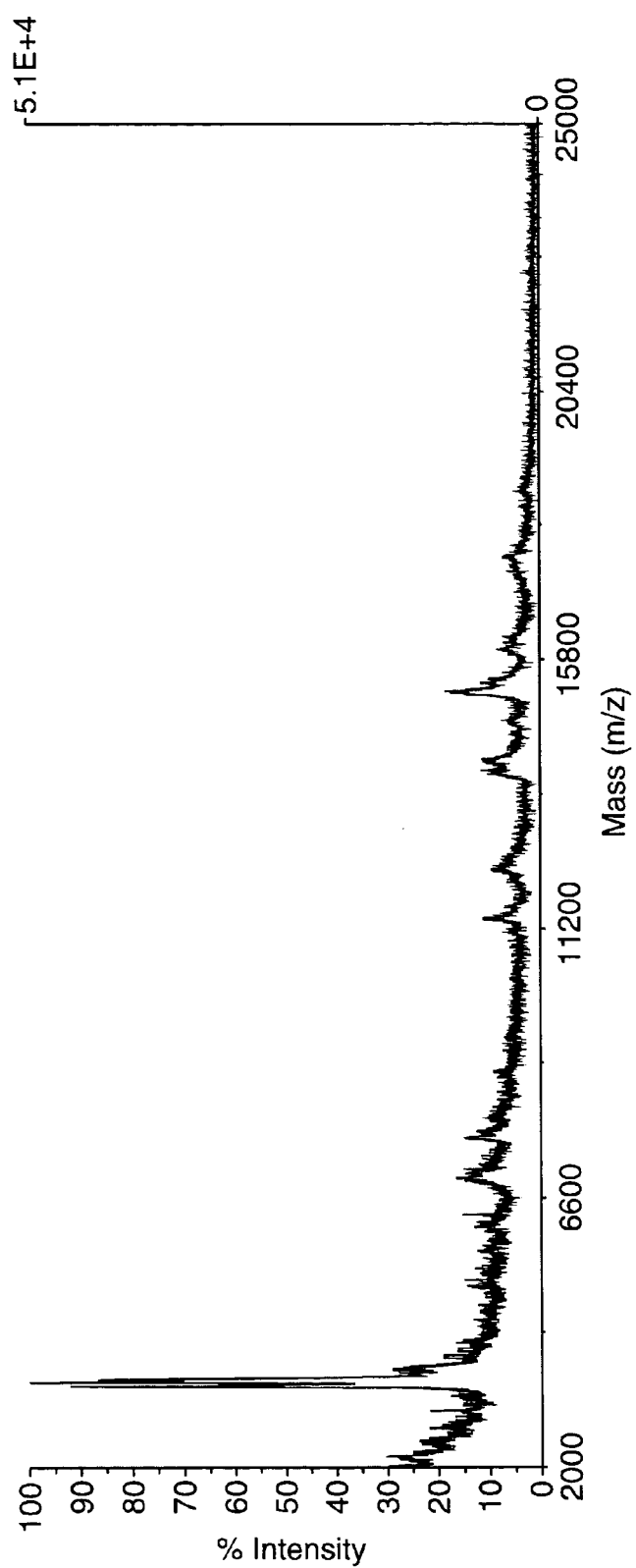
FIG. 9 is a representative graph of the mass spectra generated by Example 5, colon cancer tissue.
Figure 10:
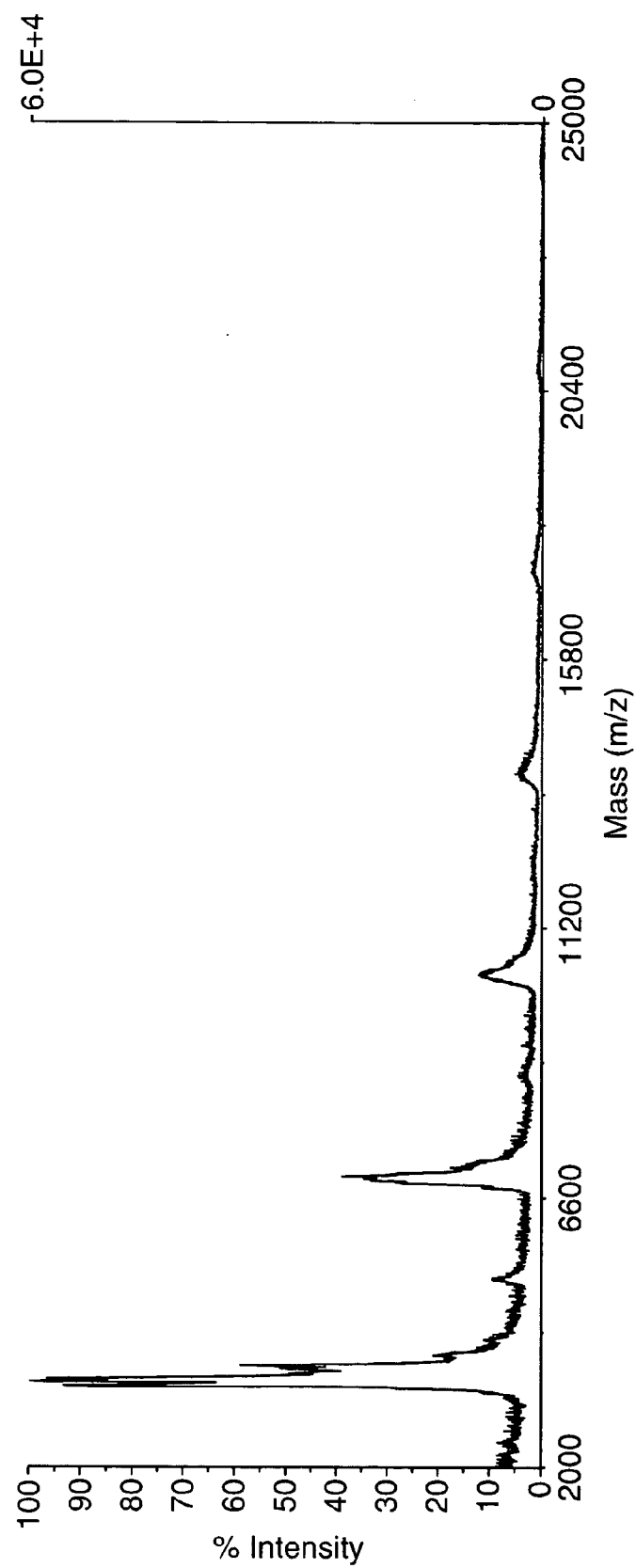
FIG. 10 is a representative graph of the mass spectra generated by Example 6, lung cancer tissue.
Figure 11:
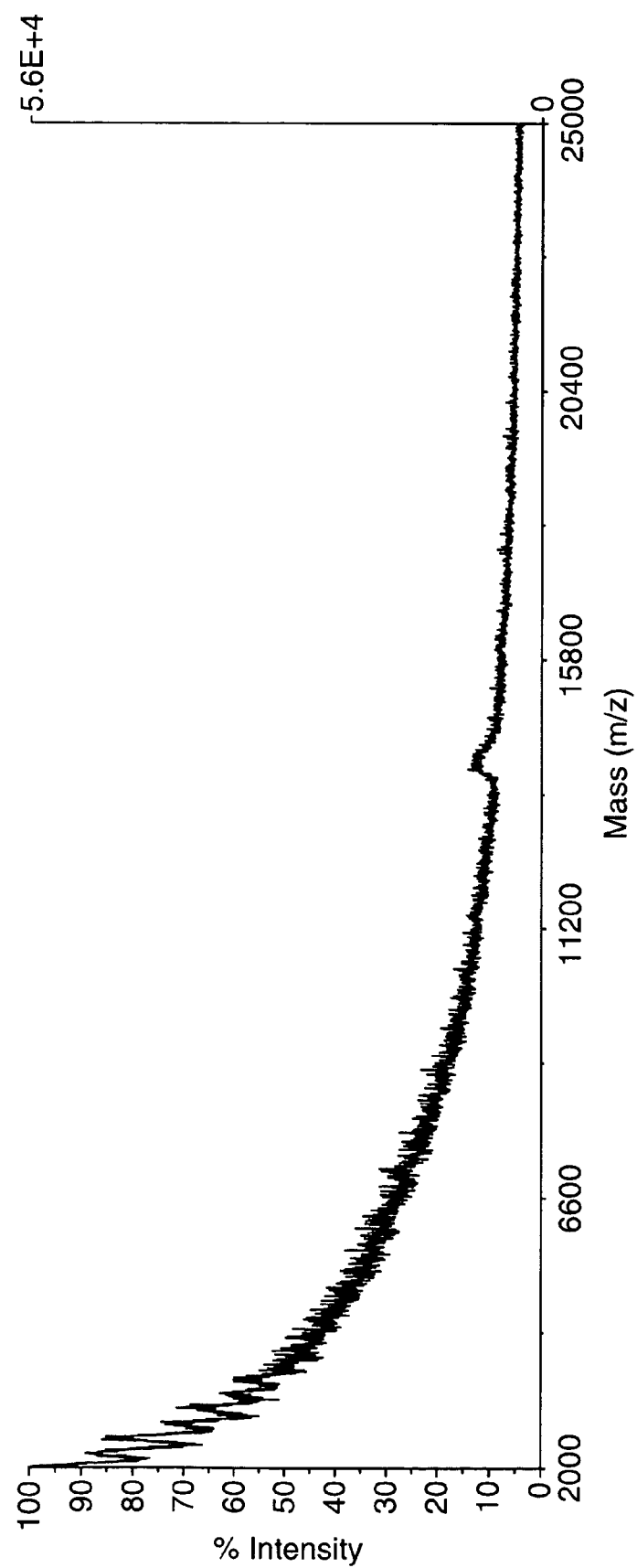
FIG. 11 is a representative graph of the mass spectra generated by Example 7, plant tissue.

FIG. 5 is a photomicrograph of the prostatic cancer tissue of example 2 and corresponds to the Protein Identification Table 3 and the mass spectra shown in FIG. 4. Likewise, FIG. 7 is a photomicrograph of the breast cancer tissue of example 3 and corresponds to the Protein Identification Table 4 and the mass spectra shown in FIG. 6.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments set forth herein and that such embodiments are presented by way of example only, with the scope of the invention intended to be limited only by the claims.

What is claimed is:

1. A method of analyzing analytes, the method comprising:
providing a cellular sample comprising chemically crosslinked analytes, wherein the sample is one or more formalin-fixed, paraffin-embedded tissue sections, and wherein the analytes are proteins or peptides or combinations thereof;
separating the chemically crosslinked analytes from the formalin-fixed, paraffin-embedded tissue sections by heat;
reversing at least a portion of the chemical crosslinks in the crosslinked analytes and forming decrosslinked analytes, wherein said reversing at least a portion of the chemical crosslinks comprises cleaving at least a portion of the chemical crosslinks, with the proviso that substantially no naturally occurring bonds in the analytes are cleaved during said reversing at least a portion of the chemical crosslinks; and analyzing the analytes by analyzing the decrosslinked analytes using mass spectrometry.

2. The method of claim 1 wherein the sample further comprises analytes that are not chemically crosslinked and analyzing both the decrosslinked analytes and the analytes that are not chemically crosslinked.

3. The method of claim 2 wherein the analytes that are not chemically crosslinked comprise pharmaceuticals, metabolites, or vitamins.

4. The method of claim 1, wherein separating the chemically crosslinked analytes from the formalin-fixed, paraffin-embedded tissue occurs prior to said reversing at least a portion of the chemical crosslinks.

5. The method of claim 1 wherein the crosslinked analytes are crosslinked proteins.

6. The method of claim 1, wherein said cleaving at least a portion of the chemical crosslinks is done through the application of an energy in the presence of water or buffer at a range of pH values.

7. The method of claim 6 wherein the energy is heat.

8. The method of claim 6 wherein the energy is radiation.

9. The method of claim 1 wherein said analyzing the decrosslinked analytes comprises cleaving at least a portion of the bonds in the decrosslinked analyte, forming analyte fragments and analyzing the analyte fragments using mass spectrometry.

10. The method of claim 9 wherein the cleaving at least a portion of the bonds in the decrosslinked analytes comprises contacting the decrosslinked analytes with an enzyme or chemical reagent.

11. The method of claim 10 wherein the cleaving at least a portion of the bonds in the decrosslinked analytes comprises contacting the decrosslinked analytes with an enzyme.

12. The method of claim 11 wherein the enzyme is selected from the group consisting of trypsin, pepsin, pronase, and chymotrypsin.

13. The method of claim 12 wherein the decrosslinked analytes are proteins, the enzyme is trypsin, and the analyte fragments are an eluate comprising protein fragments.

14. The method of claim 1 wherein the cellular sample is from a plant or animal.

15. The method of claim 14 wherein the cellular sample is from a human.

16. The method of claim 14 wherein the cellular sample is from an individual having a disease.

17. The method of claim 16 wherein the disease is a progressive disease, and the formalin-fixed, paraffin-embedded tissue sections are a plurality of tissue sections representing different stages of the progressive disease.

18. The method of claim 14 wherein the cellular sample is from a non-human animal that is model for a disease.

19. The method of claim 14 wherein the cellular sample comprises at least one cell having an exogenous nucleic acid.

20. The method of claim 1 wherein said analyzing the decrosslinked analytes comprises identifying the decrosslinked analytes.

21. The method of claim 20 wherein said identifying the decrosslinked analytes comprises:

reading unique identifiers of the decrosslinked analytes; and determining the identities of the decrosslinked analytes.

22. The method of claim 1 wherein said analyzing the decrosslinked analytes comprise quantifying the decrosslinked analytes.

23. A method of analyzing analytes, the method comprising:

providing a formalin-fixed, paraffin embedded, tissue section comprising one or more analytes comprising chemically fixed bonds;

removing the one or more analytes from the paraffin of the formalin-fixed, paraffin embedded, tissue section;

cleaving at least a portion of the chemically fixed bonds in the one or more analytes and forming cleaved analytes, with the proviso that substantially no naturally occurring bonds in the analytes are cleaved; and analyzing the analytes by analyzing the cleaved analytes using mass spectrometry, wherein the one or more analytes are proteins or peptides or combinations thereof.

24. The method of claim 23 further comprising placing the formalin—fixed, paraffin embedded, tissue section on a substrate comprising a polymeric material.

25. The method of claim 23, wherein said removing step occurs prior to said cleaving at least a portion of the chemically fixed bonds.

26. A method of analyzing an analyte, the method comprising:

providing a cellular sample comprising a chemically crosslinked analyte, wherein the sample is a formalin-fixed, paraffin-embedded tissue section;

removing the analyte from the paraffin of the formalin-fixed, paraffin embedded, tissue section;

reversing at least a portion of the chemical crosslinks in the crosslinked analyte and forming a decrosslinked analyte, wherein substantially no naturally occurring bonds in the analyte are broken during the reversal; and analyzing the analyte by analyzing the decrosslinked analyte using mass spectrometry, wherein the analyte is a protein or a peptide.

27. The method of claim 26, wherein said removing step occurs prior to said reversing a least a portion of the chemical crosslinks.

* * * * *

UNITED STATES PATENT AND TRADEMARK OFFICE
CERTIFICATE OF CORRECTION

PATENT NO. : 8,012,693 B2
APPLICATION NO. : 10/964467
DATED : September 6, 2011
INVENTOR(S) : Bathsheba E Chong Conklin Page 1 of 2

It is certified that error appears in the above-identified patent and that said Letters Patent is hereby corrected as shown below:

First Page, Column 2 (Other Documents)
Line 12          Delete "Gavin et al." and insert -- Paulse et al. --, therefor.

Page 2, Column 1 (Other Publications)
Line 11          Delete "Cyrochemistry" and insert -- Cytochemistry --, therefor.
Line 16          Delete "Cyrochemistry" and insert -- Cytochemistry --, therefor.
Line 18          Delete "Imunohistochemical" and insert -- Immunohistochemical --, therefor.
Line 66          Delete "Microdissesction" and insert -- Microdissection --, therefor.
Line 68          Delete "Nonhematorpoietic" and insert -- Nonhematopoietic --, therefor.
Line 69          Delete "Myleoproliferative" and insert -- Myeloproliferative --, therefor.

Page 2, Column 2 (Other Publications)
Line 2           Delete "Parffin" and insert -- Paraffin --, therefor.
Line 4           Delete "Microdissesction" and insert -- Microdissection --, therefor.
Line 5           Delete "Biotechniquies" and insert -- Biotechniques --, therefor.

Column 7
Line 36          Delete "athough" and insert -- although --, therefor.

Column 10
Line 44          Delete "CRYOJAN" and insert -- CRYOJANE --, therefor.

Column 15
Line 53          Delete "disc emable" and insert -- discernable --, therefor.

Column 20
Line 37 (Approx.)     Delete "Epidiymal" and insert -- Epididymal --, therefor.
Line 38 (Approx.)     After "form" insert -- precursor --.
Line 39 (Approx.)     Before "Gilal" delete "precursor".

Signed and Sealed this
Eighteenth Day of October, 2011

David J. Kappos
*Director of the United States Patent and Trademark Office*

CERTIFICATE OF CORRECTION (continued)
U.S. Pat. No. 8,012,693 B2

Line 39 (Approx.)    Delete "Gilal" and insert -- Glial --, therefor.

<u>Column 22</u>
Line 15 (Approx.)    Delete "determiningregion" and insert -- determining region --, therefor.